(12) United States Patent
Firnkes et al.

(10) Patent No.: US 10,103,004 B2
(45) Date of Patent: Oct. 16, 2018

(54) SYSTEM AND METHOD FOR IMAGING A SECONDARY CHARGED PARTICLE BEAM WITH ADAPTIVE SECONDARY CHARGED PARTICLE OPTICS

(71) Applicant: ICT Integrated Circuit Testing Gesellschaft für Halbleiterprüftechnik mbH, Heimstetten (DE)

(72) Inventors: Matthias Firnkes, Walpertskirchen (DE); Stefan Lanio, Erding (DE); Dieter Winkler, München (DE)

(73) Assignee: ICT Integrated Circuit Testing Gesellschaft für Halbleiterprüftechnik mbH, Heimstetten (DE)

( * ) Notice: Subject to any disclaimer, the term of this patent is extended or adjusted under 35 U.S.C. 154(b) by 0 days.

(21) Appl. No.: 14/790,950

(22) Filed: Jul. 2, 2015

(65) Prior Publication Data

US 2017/0003235 A1    Jan. 5, 2017

(51) Int. Cl.
*H01J 37/244*  (2006.01)
*H01J 37/26*   (2006.01)
(Continued)

(52) U.S. Cl.
CPC ............ *H01J 37/244* (2013.01); *H01J 37/09* (2013.01); *H01J 37/12* (2013.01); *H01J 37/145* (2013.01);
(Continued)

(58) Field of Classification Search
None
See application file for complete search history.

(56) References Cited

U.S. PATENT DOCUMENTS 5,644,132 A *  7/1997  Litman ............... H01J 37/244
                                              250/310
7,989,776 B2   8/2011  Müller et al.
(Continued)

FOREIGN PATENT DOCUMENTS

JP    2014026834 A *  2/2014  ............. H01J 37/09

OTHER PUBLICATIONS

U.S. Appl. No. 15/364,060 Notice of Allowance dated Dec. 21, 2017, 13 pages.
(Continued)

*Primary Examiner* — Michael Logie
(74) *Attorney, Agent, or Firm* — Kilpatrick Townsend & Stockton LLP

(57) ABSTRACT

A method of imaging a secondary charged particle beam emanating from a sample by impingement of a primary charged particle beam is provided. The method includes setting a first operating parameter to a first value. The first operating parameter is selected from a group including: landing energy of the primary charged particle beam on the sample, extraction field strength for the secondary charged particle beam at the sample, magnetic field strength of an objective lens that focuses the primary charged particle beam onto the sample, and working distance of the objective lens from the sample. The method further includes controlling, while the first operating parameter is set to the first value, the excitation of a first lens and of a second lens to map the secondary charged particle beam onto a first region on an aperture plate. The first region overlaps with a first opening of the aperture plate and with a second opening of the aperture plate. The method further includes setting the first operating parameter to a second value different from the first value. The method further includes controlling, while the first operating parameter is set to the second value, the (Continued)

excitation of the first lens and of the second lens to map the secondary charged particle beam onto the first region on the aperture plate.

4 Claims, 10 Drawing Sheets

(51) Int. Cl.
  *H01J 37/22* (2006.01)
  *H01J 37/09* (2006.01)
  *H01J 37/12* (2006.01)
  *H01J 37/145* (2006.01)
(52) U.S. Cl.
  CPC ............ *H01J 37/222* (2013.01); *H01J 37/26* (2013.01); *G01N 2223/418* (2013.01); *G01N 2223/6116* (2013.01); *H01J 2237/0453* (2013.01); *H01J 2237/1202* (2013.01); *H01J 2237/2448* (2013.01)

(56) References Cited

U.S. PATENT DOCUMENTS

| | | |
|---|---|---|
| 8,124,940 B2 | 2/2012 | Shigeto et al. |
| 2002/0088940 A1* | 7/2002 | Watanabe ............. H01J 37/224 250/310 |
| 2002/0142496 A1* | 10/2002 | Nakasuji ............... G01N 23/225 438/14 |
| 2005/0104017 A1* | 5/2005 | Kimba ................... G06T 7/001 250/559.07 |
| 2012/0074316 A1* | 3/2012 | Watanabe ............. H01J 37/265 250/307 |
| 2012/0193530 A1* | 8/2012 | Parker ................ G01N 21/6428 250/307 |
| 2013/0270438 A1* | 10/2013 | Lanio ..................... H01J 37/09 250/310 |
| 2013/0320228 A1* | 12/2013 | Lanio .................... H01J 37/244 250/397 |
| 2014/0175277 A1* | 6/2014 | Lanio .................... H01J 37/261 250/307 |
| 2014/0312227 A1* | 10/2014 | Yoshikawa ........ G01N 23/2204 250/310 |
| 2015/0021474 A1* | 1/2015 | Firnkes ................... H01J 37/10 250/306 |
| 2015/0083910 A1* | 3/2015 | Nomaguchi .......... H01J 37/244 250/310 |
| 2016/0268096 A1* | 9/2016 | Ren ..................... H01J 37/1474 |
| 2017/0076910 A1 | 3/2017 | Firnkes et al. |

OTHER PUBLICATIONS

U.S. Appl. No. 15/364,060 Non-Final Office Action dated Sep. 7, 2017, 10 pages.

* cited by examiner

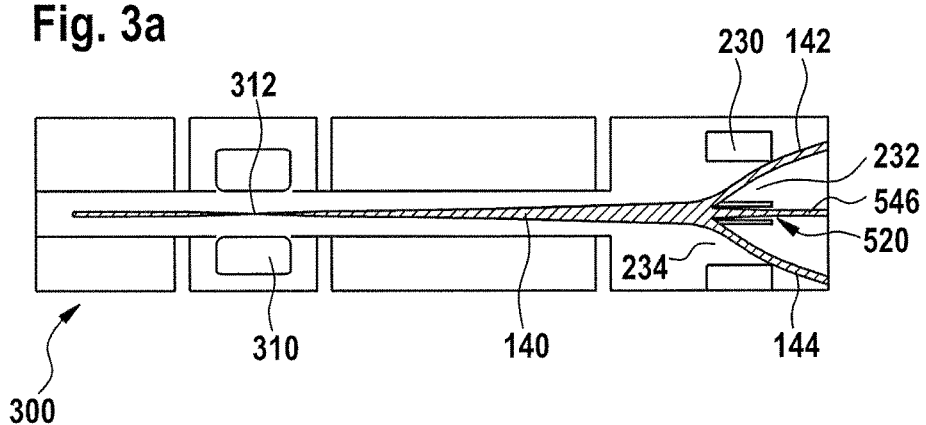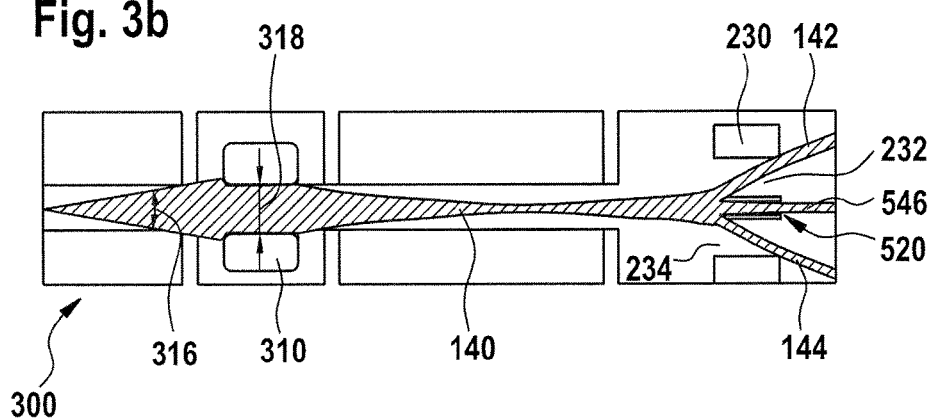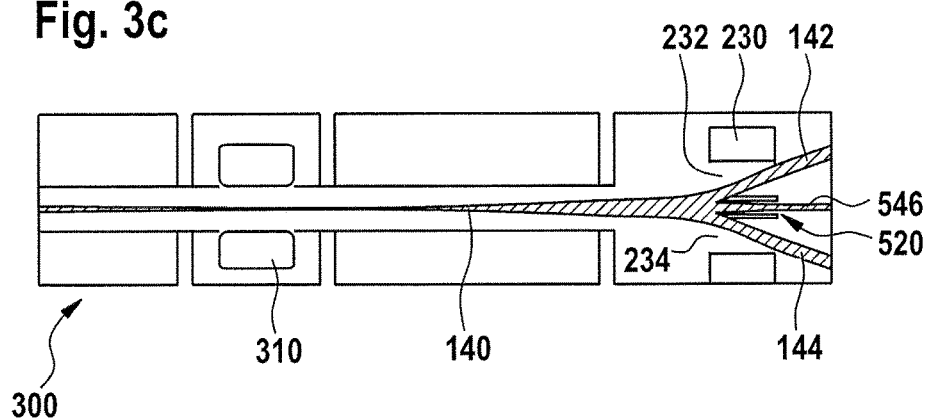

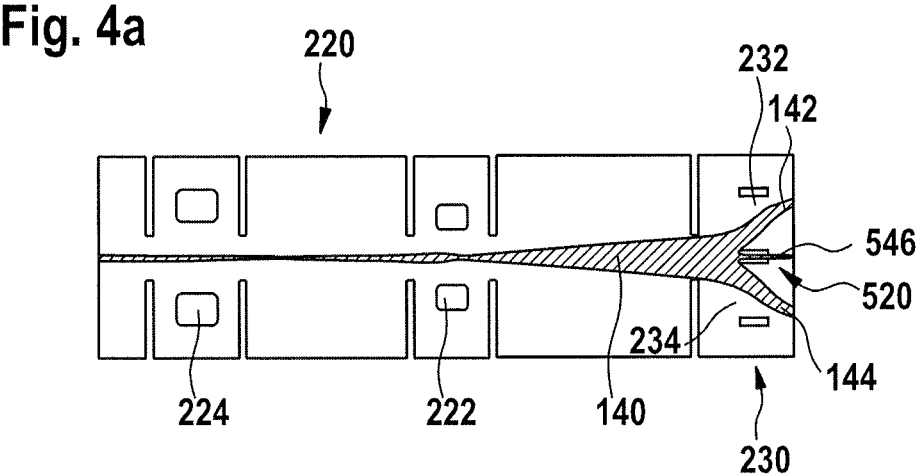
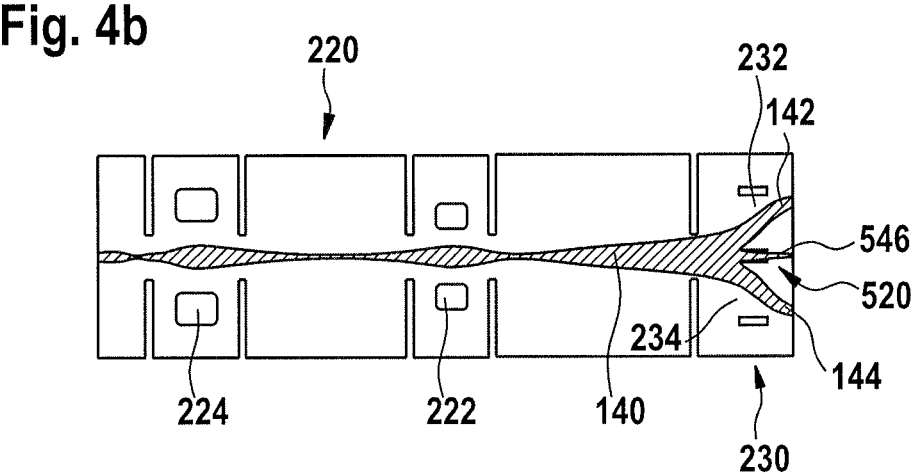
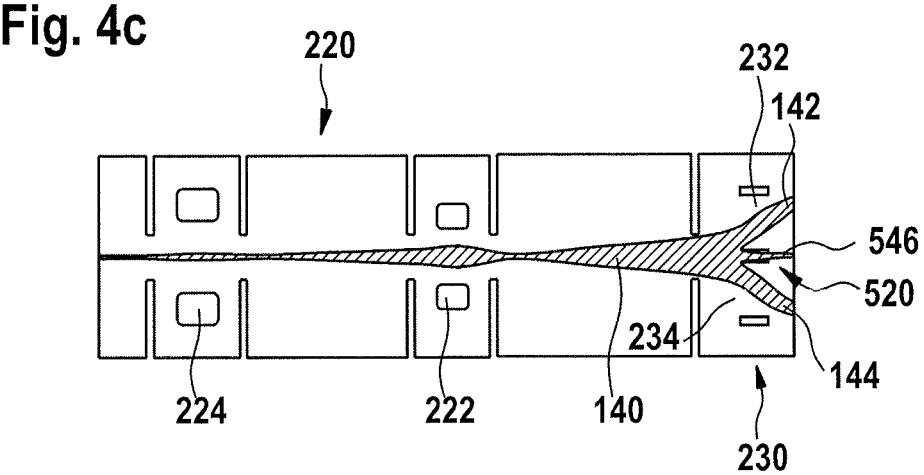

SYSTEM AND METHOD FOR IMAGING A SECONDARY CHARGED PARTICLE BEAM WITH ADAPTIVE SECONDARY CHARGED PARTICLE OPTICS

FIELD

Embodiments described herein relate to charged particle beam devices, specifically to secondary charged particle imaging systems, for example, for inspection system applications, testing system applications, lithography system applications, defect review or critical dimensioning applications, or the like. Embodiments described herein also relate to methods of operating such devices and systems, and to methods of imaging a secondary charged particle beam. Further embodiments described herein relate to applications having a charged particle path for secondary particles, e.g. for electron beam inspection (EBI).

BACKGROUND

Charged particle beam apparatuses have many functions in a plurality of industrial fields, including, but not limited to, inspection of semiconductor devices during manufacturing, exposure systems for lithography, detecting devices and testing systems. Thus, there is a high demand for structuring and inspecting specimens within the micrometer and nanometer scale.

Micrometer and nanometer scale process control, inspection or structuring, is often done with charged particle beams, e.g. electron beams, which are generated and focused in charged particle beam devices, such as electron microscopes or electron beam pattern generators. Charged particle beams offer superior spatial resolution compared to, e.g. photon beams due to their short wavelengths.

Besides resolution, throughput is an issue with such devices. Since large substrate areas have to be patterned or inspected, throughput of, for example, larger than 10 $cm^2$/min is desirable. In charged particle beam devices, the throughput depends quadratically on the image contrast. Thus, there is a need for contrast enhancement.

Particle detectors, e.g. electron detectors, for particle beam systems, e.g. electron microscopes, can be used for electron beam inspection (EBI), defect review (DR) or critical dimension (CD) measurement, focused ion beam systems (FIB) or the like. Upon irradiation of a sample by a primary beam of electrons, secondary particles, e.g. secondary electrons (SE), are created, which carry information about the topography of the sample, its chemical constituents, its electrostatic potential and others. In a simple detector, all of the SE are collected and guided to a sensor. An image is created where the gray level is proportional to the number of electrons collected.

High resolution electron optics systems may benefit from a short working distance between the objective lens and the sample. Secondary electron collection is therefore typically done inside the column above the objective lens. A configuration commonly found in prior-art electron-beam imaging systems is shown schematically in FIG. 1. A column with length 104, including a beam emitter 105, an objective lens 10 and a detector 115 are spaced at a working distance 120 from a sample 125. The detector 115 shown in FIG. 1 is an annular secondary-electron detector. Primary charged particle beam 130 emitted from beam emitter 105 is directed at sample 125 through an opening 135 in detector 115. A secondary charged particle beam 140, e.g. a secondary electron beam, is emitted from sample 125 in a broad cone surrounding primary charged particle beam 130. Some of the secondary electrons are collected by detector 115 to produce a secondary-electron (SE) signal 145.

Moreover, it is desired for many applications that the imaging information is increased while high-speed detection is provided. For example, upon irradiation of a sample by a primary beam of electrons, secondary electrons (SE) are created which carry information about the topography of the sample, its chemical constituents, its electrostatic potential and others. High speed detection provided with topography information and/or information on the energy of the secondary particles is a challenging task, for which continuous improvement is desired. Accordingly, improvements of the detection in the SEM-based tools, particularly in high throughput defect inspection or review tools are desired. Additionally or alternatively, separation of several signal beam bundles, e.g. with reduced cross-talk, is desired for the topography detection mode where topography information is imaged.

Further, a charged particle beam device may be operated with operating parameters, such as working distance, strength of the magnetic field of the objective lens etc., varying in certain ranges, called the operating window hereinafter. It is desirable that good images can be obtained throughout this operating window, in particular in connection with the topography detection mode.

SUMMARY

According to an embodiment, a method of imaging a secondary charged particle beam emanating from a sample by impingement of a primary charged particle beam is provided. The method includes setting a first operating parameter to a first value. The first operating parameter is selected from a group including: landing energy of the primary charged particle beam on the sample, extraction field strength for the secondary charged particle beam at the sample, magnetic field strength of an objective lens that focuses the primary charged particle beam onto the sample, and working distance of the objective lens from the sample. The method further includes controlling, while the first operating parameter is set to the first value, the excitation of a first lens and of a second lens to map the secondary charged particle beam onto a first region on an aperture plate. The first region overlaps with a first opening of the aperture plate and with a second opening of the aperture plate. The method further includes setting the first operating parameter to a second value different from the first value. The method further includes controlling, while the first operating parameter is set to the second value, the excitation of the first lens and of the second lens to map the secondary charged particle beam onto the first region on the aperture plate.

According to another embodiment, a secondary charged particle imaging system for imaging a secondary charged particle beam emanating from a sample by impingement of a primary charged particle beam is provided. The system includes a detector arrangement and adaptive secondary charged particle optics. The detector arrangement includes a first detection element for detecting a first secondary charged particle sub-beam of the secondary charged particle beam in a topography detection mode. The detector arrangement further includes a second detection element for detecting a second secondary charged particle sub-beam of the secondary charged particle beam in the topography detection mode. The first detection element and the second detection element are separated from each other. The adaptive secondary charged particle optics includes an aperture plate including a first opening for letting the first secondary charged particle sub-beam pass through and a second opening for letting the second secondary charged particle sub-beam pass through. The adaptive secondary charged particle optics further includes a lens system for mapping the secondary charged particle beam onto the aperture plate, the lens system including a first lens and a second lens. The adaptive secondary charged particle optics further includes a controller for controlling the excitation of the first lens and the excitation of the second lens. With respect to the propagation of the secondary charged particle beam, the aperture plate is arranged upstream of the detector arrangement, the first lens is arranged upstream of the aperture plate, and the second lens is arranged upstream of the first lens. The controller is configured to independently control the excitation of the first lens and of the second lens to map the secondary charged particle beam onto the aperture plate so that the first secondary charged particle sub-beam passes through the first opening and the second secondary charged particle sub-beam passes through the second opening in the topography detection mode independent of a variation of at least one first operating parameter. The at least one first operating parameter is selected from a group comprising: landing energy of the primary charged particle beam on the sample, extraction field strength for the secondary charged particle beam at the sample, magnetic field strength of an objective lens that focuses the primary charged particle beam onto the sample, and working distance of the objective lens from the sample.

According to another embodiment, a charged particle beam device is provided. The charged particle beam device includes an emitter for emitting a primary charged particle beam. The charged particle beam device further includes an objective lens for focusing the primary charged particle beam onto a sample. The charged particle beam device further includes a beam separator for separating the primary charged particle beam from a secondary charged particle beam emanating from the sample. The charged particle beam device further includes a secondary charged particle beam imaging system for imaging the secondary charged particle beam. With respect to the propagation of the secondary charged particle beam, the secondary charged particle beam imaging system is arranged downstream of the beam separator. The secondary charged particle beam imaging system includes a detector arrangement and adaptive secondary charged particle optics. The detector arrangement includes a first detection element for detecting a first secondary charged particle sub-beam of the secondary charged particle beam in a topography detection mode. The detector arrangement further includes a second detection element for detecting a second secondary charged particle sub-beam of the secondary charged particle beam in the topography detection mode. The first detection element and the second detection element are separated from each other. The adaptive secondary charged particle optics includes an aperture plate including a first opening for letting the first secondary charged particle sub-beam pass through and a second opening for letting the second secondary charged particle sub-beam pass through. The adaptive secondary charged particle optics further includes a lens system for mapping the secondary charged particle beam onto the aperture plate, the lens system including a first lens and a second lens. The adaptive secondary charged particle optics further includes a controller for controlling the excitation of the first lens and the excitation of the second lens. With respect to the propagation of the secondary charged particle beam, the aperture plate is arranged upstream of the detector arrangement, the first lens is arranged upstream of the aperture plate, and the second lens is arranged upstream of the first lens. The controller is configured to independently control the excitation of the first lens and of the second lens to map the secondary charged particle beam onto the aperture plate so that the first secondary charged particle sub-beam passes through the first opening and the second secondary charged particle sub-beam passes through the second opening in the topography detection mode independent of a variation of at least one first operating parameter. The at least one first operating parameter is selected from a group comprising: landing energy of the primary charged particle beam on the sample, extraction field strength for the secondary charged particle beam at the sample, magnetic field strength of an objective lens that focuses the primary charged particle beam onto the sample, and working distance of the objective lens from the sample.

According to another embodiment, a secondary charged particle imaging system for imaging a secondary charged particle beam emanating from a sample by impingement of a primary charged particle beam is provided. The system includes a detector arrangement and adaptive secondary charged particle optics. The detector arrangement includes a first detection element for detecting a first secondary charged particle sub-beam of the secondary charged particle beam in a topography detection mode. The detector arrangement further includes a second detection element for detecting a second secondary charged particle sub-beam of the secondary charged particle beam in the topography detection mode. The first detection element and the second detection element are separated from each other. The adaptive secondary charged particle optics includes an aperture plate including a first opening for letting the first secondary charged particle sub-beam pass through and a second opening for letting the second secondary charged particle sub-beam pass through. The adaptive secondary charged particle optics further includes a lens system for mapping the secondary charged particle beam onto the aperture plate. The lens system includes a first lens, wherein the first lens includes a magnetic lens portion for compensating the Larmor rotation of an objective lens that focuses the primary charged particle beam onto the sample. The adaptive secondary charged particle optics further includes a controller for controlling the excitation of the first lens. With respect to the propagation of the secondary charged particle beam, the aperture plate is arranged upstream of the detector arrangement, and the first lens is arranged upstream of the aperture plate. The controller is configured to control the excitation of the first lens, including controlling the excitation of the magnetic lens portion, to map the secondary charged particle beam onto the aperture plate so that the first secondary charged particle sub-beam passes through the first opening and the second secondary charged particle sub-beam passes through the second opening in the topography detection mode independent of a variation in a magnetic field strength of the objective lens.

Embodiments are also directed to methods for operating the disclosed systems and devices, and to the use of the disclosed system to perform the methods according to embodiments described herein. The method may be performed manually or automated, e.g. controlled by a computer programmed by appropriate software, by any combination of the two or in any other manner.

Further advantages, features, aspects and details that can be combined with embodiments described herein are evident from the dependent claims, the description and the drawings.

BRIEF DESCRIPTION OF THE DRAWINGS

A full and enabling disclosure to one of ordinary skill in the art is set forth more particularly in the remainder of the specification including reference to the accompanying drawings wherein:

FIGS. 3a-c show examples of a secondary optics including a single lens;

FIGS. 4a-c illustrate embodiments where a charged particle beam device, according to embodiments described herein, is operated in a topography detection mode for different values of the landing energy and of the extraction field strength;

FIG. 14 illustrates a method of imaging a secondary charged particle beam according to embodiments described herein.

DETAILED DESCRIPTION

Figure 1:
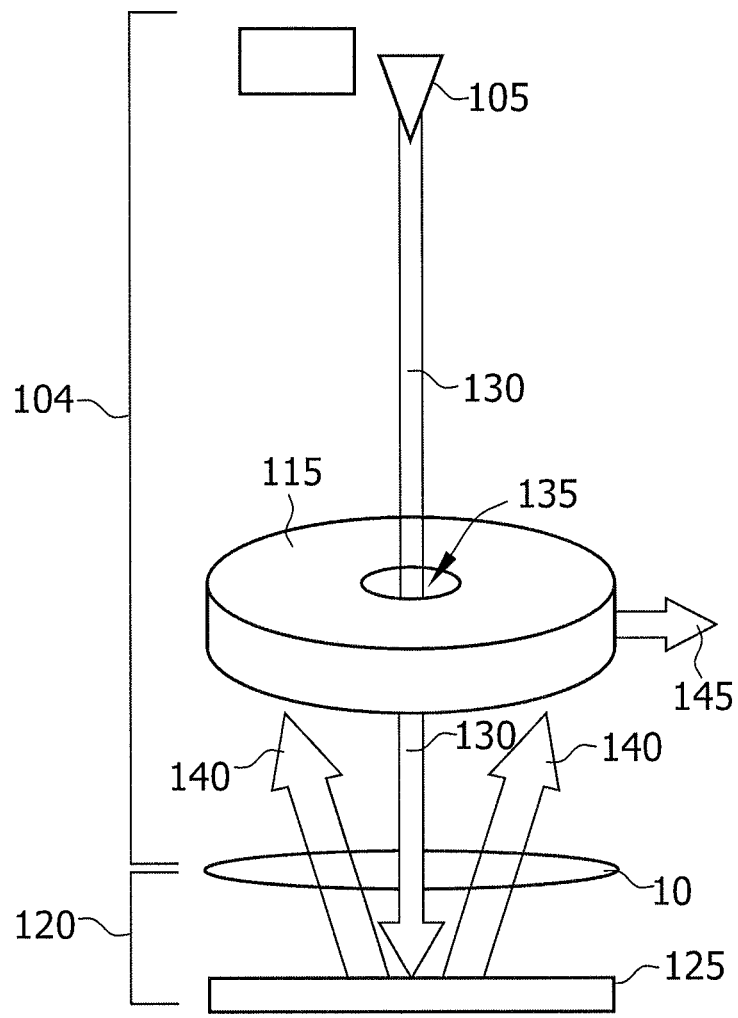
FIG. 1 shows a known electron beam imaging system.

Reference will now be made in detail to the various exemplary embodiments, one or more examples of which are illustrated in each figure. Each example is provided by way of explanation and is not meant as a limitation. For example, features illustrated or described as part of one embodiment can be used on or in conjunction with other embodiments to yield yet further embodiments. It is intended that the present disclosure includes such modifications and variations.

Within the following description of the drawings, the same reference numbers refer to the same components. Generally, only the differences with respect to the individual embodiments are described. The structures shown in the drawings are not necessarily depicted true to scale but rather allow for a greater understanding of the embodiments.

The term "sample", as used herein, may include, but is not limited to, semiconductor wafers, semiconductor workpieces, and other workpieces such as memory disks and the like. Embodiments may be applied to any workpiece on which material is deposited, which is inspected or which is structured. A sample may include a surface to be structured, imaged or on which layers are deposited. The term "charged particles", as used herein, may include electrons, ions, atoms, or other charged particles. The term "primary charged particles" refers to charged particles being emitted by a beam emitter and being directed onto a sample. The term "secondary charged particles" refers to charged particles created at or in the sample, and/or backscattered charged particles. Secondary electrons may also be referred to as signal electrons. Signal electrons may include electrons created in or at the sample, backscattered electrons and/or Auger electrons. Accordingly, the term "secondary charged particles", as used herein, may also refer to or may be replaced by "signal charged particles".

The terminology of "shaping" a charged particle beam, as described herein, may include adjusting a divergence of the charged particle beam. The terminology of "focusing" a charged particle beam, as described herein, may refer to reducing a divergence of the charged particle beam. The charged particles of a beam may be focused or at least collimated towards a subsequent beam optical element to decrease losses of charged particles due to divergence or due to blocking of charged particles. Correspondingly, "defocusing" may be understood as increasing the divergence.

Figure 2A:
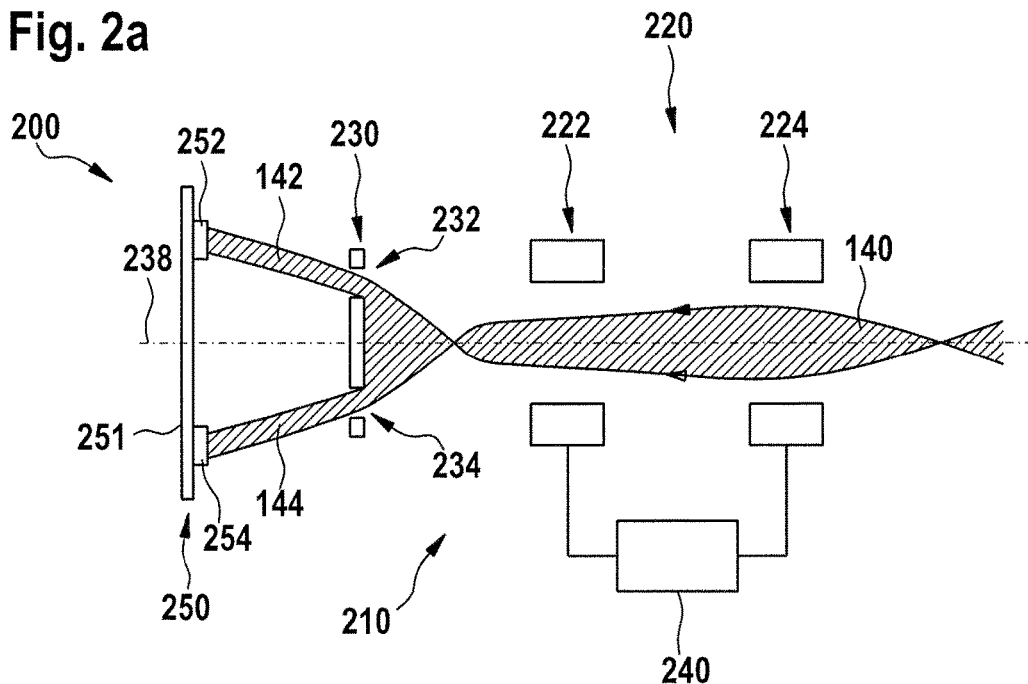
FIG. 2a shows a secondary charged particle imaging system according to embodiments described herein.

Embodiments described herein relate to a secondary charged particle imaging system allowing for high-speed topography measurements of a secondary charged particle beam, wherein a good image quality is provided independent of varying one or more operating parameters of the system across an operation window. FIG. 2a shows a secondary charged particle imaging system 200 according to embodiments described herein. The secondary charged particle imaging system 200 is adapted for imaging a secondary charged particle beam 140. The secondary charged particle imaging system 200 is shown in a state of operation according to which the secondary charged particle beam 140 is imaged in a topography detection mode.

The secondary charged particle imaging system 200 includes an adaptive secondary charged particle optics 210 including a lens system 220, an aperture plate 230 and a controller 240. The lens system 220 includes a first lens 222 and a second lens 224. As shown in FIG. 2a, the first lens 222 may be distanced from the second lens 224. The distance between the first lens and the second lens may be in the range from 40 to 200 mm.

The aperture plate 230 includes a first opening 232 and a second opening 234. As shown in FIG. 2a, the first opening 232 may be distanced from the second opening 234. As further shown, the aperture plate 230 may be arranged parallel to the first lens 222 and/or to the second lens 224. With respect to the drawing plane of FIG. 2a, the first lens 222, the second lens 224 and the aperture plate 230 extend along a vertical ("up-down") direction. As shown, the first opening 232 may be formed, with respect to the vertical direction, at an upper portion of the aperture plate 230. The second opening 234 may be formed at a lower portion of the aperture plate 230. The aperture plate 230 may define an optical axis 238. As discussed in further detail below, the optical axis 238 may extend through a center of the aperture plate 230. With respect to the drawing plane of FIG. 2a, the optical axis 238 shown in FIG. 2a extends along a horizontal ("left-right") direction perpendicular to the vertical direction. As illustrated in FIG. 2a, the aperture plate 230 may be distanced from the first lens 222 and/or from the second lens 224. The distance between the center of the aperture plate and the center of the first lens may be in the range from 40 to 200 mm. As further shown in FIG. 2a, the first lens 222 may be arranged between the aperture plate 230 and the second lens 224.

The secondary charged particle imaging system 200 shown in FIG. 2a further includes a detector arrangement 250 including a first detection element 252 and a second detection element 254. As illustrated in FIG. 2a, the second detection element 254 may be distanced from the first detection element 252. As further shown, the first detection element 252 and the second detection element 254 may be supported by a holder 251 of the detector arrangement 250. The holder 251 may include a holder plate on which the first detection element 252 and/or the second detection element 254 are attached. The aperture plate 230, the first lens 222 and/or the second lens 224 may be parallel to a plane defined by the detector arrangement 250 and/or defined by the holder 251. The first detection element 252 shown in FIG. 2a is arranged, with respect to the vertical direction, at an upper portion of the detector arrangement 250. The second detection element 254 shown in FIG. 2a is arranged at a lower portion of the detector arrangement 250. The first detection element 252 and the first opening 232 may be arranged on a first side of a reference plane containing the optical axis 238. The second detection element 254 and the second opening 234 may be arranged on a second side of the reference plane, wherein the second side is opposite to the first side.

In the drawing plane of FIG. 2a, the secondary charged particle beam 140 travels from right to left. The secondary charged particle beam 140 enters the second lens 224 of the lens system 220 from the right-hand side of the second lens 224. The secondary charged particle beam 140 shown in FIG. 2a travels through the second lens 224 and subsequently through the first lens 222 of the lens system 220. As shown, the secondary charged particle beam 140 traveling through the lens system 220 travels substantially along the optical axis 238.

The first lens 222 and/or the second lens 224 may be adapted for shaping, focusing and/or defocusing the secondary charged particle beam 140. The first lens 222 and/or the second lens 224 may be adapted for adjusting an opening angle of the secondary charged particle beam 140. The secondary charged particle beam 140 can be made divergent or convergent as desired. Accordingly, collection efficiency of secondary charged particles by the detector arrangement 250 can be improved. An opening angle of the secondary charged particle beam 140 may be an opening angle of the secondary charged particle beam 140 exiting a beam bender arranged upstream, with respect to the propagation of the secondary charged particle beam 140, of the lens system 220, as discussed in greater detail below.

The lens system 220 may be adapted for providing one or two cross-overs of the secondary charged particle beam 140. Alternatively, the lens system may be adapted for allowing the secondary charged particle beam to pass through the secondary charged particle imaging system 200 without a cross-over.

The first lens 222 may include an electrostatic lens portion and/or a magnetic lens portion. The first lens 222 may be a compound lens including both an electrostatic lens portion and a magnetic lens portion. Similarly, the second lens 224 may include an electrostatic lens portion and/or a magnetic lens portion. An electrostatic lens portion of the first lens 222 and/or an electrostatic lens portion of the second lens 224 may be adapted for shaping, focusing and/or defocusing the secondary charged particle beam. As discussed in further detail below, a magnetic lens portion of the first lens 222 and/or of the second lens 224 may be adapted for compensating a Larmor rotation of an objective lens.

As further shown in FIG. 2a, the signal charged particle beam or secondary charged particle beam 140 may travel from the first lens 222 to the aperture plate 230. The lens system 220 is adapted for mapping the secondary charged particle beam 140 onto the aperture plate 230. The first lens 222 and the second lens 224 may be adapted for individually shaping, focusing and/or defocusing the secondary charged particle beam 140 so that the secondary charged particle beam 140 is mapped onto the aperture plate 230. The terminology that the secondary charged particle beam is "mapped" onto the aperture plate, as used herein, may refer to a secondary charged particle beam being directed, guided and/or provided onto the aperture plate.

As illustrated in FIG. 2a, in the topography detection mode of the secondary charged particle imaging system 200, the secondary charged particle beam 140 passes through the first opening 232 and through the second opening 234 of the aperture plate 230. The secondary charged particle beam 140 may be shaped by the first lens 222 and/or by the second lens 224 so that the secondary charged particle beam 140 traveling from the lens system 220 to the aperture plate 230 is slightly divergent. Accordingly, passage of the secondary charged particle beam 140 through the first opening 232 and through the second opening 234 may be facilitated. The aperture plate 230 may include an electrode. The electrode may be a separation electrode adapted for separating the secondary charged particle beam into secondary charged particle sub-beams. A voltage may be applied to the electrode for generating a deceleration field at or near the aperture plate 230. Under the influence of the deceleration field, the secondary charged particles traveling from the lens system 220 to the aperture plate 230 may be decelerated as the secondary charged particles approach the aperture plate 230. An advantage of decelerating the secondary charged particles approaching the aperture plate 230 is that the secondary charged particles are more easily deflected towards the openings in the aperture plate 230, e.g. towards the first opening 232 and the second opening 234. The deceleration field may provide an energy filter, wherein secondary charged particles having energies lying in a prescribed energy range, e.g. energies lying above a prescribed threshold energy value, may pass through the openings of the aperture plate in the topography detection mode. Providing an energy filter of the secondary charged particle beam may enhance the sensitivity of the system to changes in the surface potential applied to the sample (voltage contrast—VC).

In the topography detection mode of the secondary charged particle imaging system 200, a first sub-beam 142 of the secondary charged particle beam 140 passes through the first opening 232. The first sub-beam 142 travels from the first opening 232 to the first detection element 252. The first sub-beam 142 is subsequently detected by the first detection element 252 in the topography detection mode. Similarly, in the topography detection mode, a second sub-beam 144 passes through the second opening 234. The second sub-beam 144 travels from the second opening 234 to the second detection element 254. The second sub-beam 144 is subsequently detected by the second detection element 254 in the topography detection mode.

The secondary charged particles of the first sub-beam 142 and/or of the second sub-beam 144, and of potential other sub-beams of the secondary charged particle beam 140 traveling from the aperture plate 230 to the detector arrangement 250, may be accelerated by an acceleration field generated between the aperture plate 230 and the detector arrangement 250. The secondary charged particles may be accelerated to substantially the same energy as the secondary charged particles leaving the lens system 220 prior to entering the deceleration field at the aperture plate 230. Accelerating the secondary charged particles approaching the detector arrangement 250 may provide a focusing effect which allows focusing the sub-beams of the secondary charged particle beam 140 onto the corresponding detection elements. Accordingly, topography contrast and bright field imaging can be achieved simultaneously (multi perspective imaging).

The controller 240 shown in FIG. 2a may be configured for controlling the excitation of the first lens 222 and the excitation of the second lens 224. Controlling the excitation of the first lens 222 may include controlling the excitation of an electrostatic lens portion of the first lens 222 and/or controlling the excitation of a magnetic lens portion of the first lens 222. Similar considerations apply to the case where the second lens 224 includes an electrostatic and/or magnetic lens portion.

An electrostatic lens portion of the first lens 222 may include one or more electrodes for generating an electric field. A potential may be applied to the electrodes for generating the electric field. The electric field may be generated under the control of the controller 240. In particular, the strength of the electric field may be controlled by, determined by and/or adjusted under the control of the controller 240. A magnetic lens portion of the first lens 222 may each include one or more coils for generating a magnetic field. A current may be passed through the coils for generating the magnetic field. The magnetic field may be generated under the control of the controller 240. In particular, the strength of the magnetic field as well as the field direction determined by the current direction through the coils may be controlled by, determined by and/or adjusted under the control of the controller 240. Similar considerations apply to an electrostatic lens portion and/or magnetic lens portion included in the second lens 224. According to embodiments described herein, the first lens may include an electrostatic lens portion, a magnetic lens portion, or both, an electrostatic lens portion and a magnetic lens portion. According to embodiments described herein, the second lens may include an electrostatic lens portion, a magnetic lens portion, or both, an electrostatic lens portion and a magnetic lens portion. Providing a combined electrostatic magnetic lens for the first and/or second lens, i.e. having an electrostatic lens portion and a magnetic lens portion, may allow for increased degrees of freedom in adjusting the signal charged particle beam, particularly with respect to Larmor rotation as described below.

The controller 240 may be configured for independently controlling the excitation of the first lens 222 and of the second lens 224. Accordingly, the controller 240 may allow controlling the focusing, defocusing and/or shaping of the secondary charged particle beam 140 by the first lens 222 independently of controlling the focusing, defocusing and/or shaping of the secondary charged particle beam 140 by the second lens 224. Independently controlling the excitations of the first lens 222 and of the second lens 224 provides that, in the topography detection mode of the secondary charged particle imaging system 200, the first sub-beam 142 passes through the first opening 232 and is detected by the first detection element 252 and that the second sub-beam 144 passes through the second opening 234 and is detected by the second detection element 254.

Figure 2B:
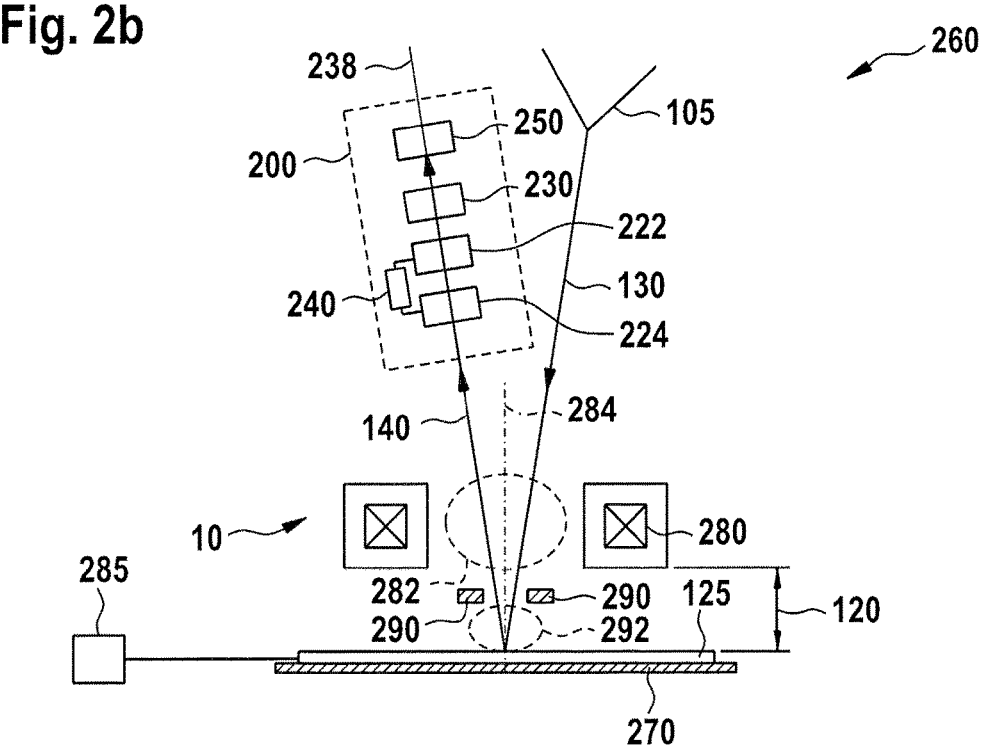
FIG. 2b shows a charged particle beam device according to embodiments described herein.

FIG. 2b shows a charged particle beam device 260 including a secondary charged particle imaging system 200 according to embodiments described herein. The charged particle beam device 260 shown in FIG. 2b includes a beam emitter 105. As shown in FIG. 2b, a primary charged particle beam 130 is emitted by the beam emitter 105 and directed onto a sample 125 disposed on a stage 270. The charged particle beam device 260 shown in FIG. 2b further includes an objective lens 10. The objective lens 10 may be configured for focusing the primary charged particle beam 130 onto the sample 125. As shown in FIG. 2b, the objective lens may include a magnetic objective lens portion 280 for generating a magnetic field 282. As further shown in FIG. 2b, the magnetic field 282 may act on the primary charged particle beam 130 passing through the objective lens 10. Under the influence of the magnetic field 282, the primary charged particle beam 130 may be focused by the objective lens 10. The magnetic field 282 may be an adjustable magnetic field. By adjusting the strength of the magnetic field 282, a divergence of the primary charged particle beam 130 may be adjusted to focus the primary charged particle beam 130 onto the sample 125. Alternatively or additionally to the magnetic objective lens portion 280, the objective lens 10 may include an electrostatic objective lens portion (not shown) configured for generating an electric field acting on the primary charged particle beam 130 to facilitate focusing the primary charged particle beam 130 onto the sample 125.

As further shown in FIG. 2b, the objective lens 10 may define an optical axis 284. The optical axis 284 may be perpendicular to a plane defined by the sample 125 and/or to a plane defined by the stage 270. The objective lens 10 may be arranged at a working distance 120 from the sample 125. As shown in FIG. 2b, the working distance 120 may refer to a distance, e.g. in a direction parallel to the optical axis 284 defined by the objective lens 10, between the objective lens 10 and the sample 125.

The working distance 120 may be an adjustable working distance. The working distance 120 may be adjusted by displacing the stage 270 with respect to the objective lens 10, e.g. in a direction parallel to the optical axis 284. For example, in the embodiment illustrated in FIG. 2b, the objective lens 10 may be arranged in a fixed position in the charged particle beam device 260 and the working distance 120 may be adjusted by moving the stage 270 in a direction parallel to the optical axis 284. By adjusting the working distance 120, the position of the sample 125 with respect to the objective lens 10 may be adjusted for improving the imaging.

As further shown in FIG. 2b, the charged particle beam device 260 may include a sample voltage source 285. The sample voltage source 285 may be configured for applying a sample voltage to the sample 125 to adjust a landing energy of the primary charged particle beam 130 on the sample 125. The landing energy may be adjusted in order to probe the sample 125 at different energies and to potentially resolve different structures on the sample 125. As used herein, the term "landing energy" may refer to the energy, e.g. the average energy, of the primary charged particle beam upon impinging onto the sample. The value of the sample voltage affects the strength of an electric force accelerating or decelerating the primary charged particles with respect to the sample. Accordingly, adjusting the value of the sample voltage allows for adjusting the landing energy of the primary charged particle beam.

As further shown in FIG. 2b, the charged particle beam device 260 may include one or more proxi electrodes 290 which may be arranged between the stage 270 and the objective lens 10. The proxi electrodes 290 may provide an extraction field 292, as illustrated in FIG. 2b. As shown in FIG. 2b, the extraction field 292 may influence the secondary charged particle beam 140. By adjusting the strength of the extraction field 292, the acceleration of the secondary charged particle beam 140 leaving the sample 125 may be adjusted.

As further shown in FIG. 2b, the secondary charged particle beam 140 traveling from the sample 125 to the secondary charged particle imaging system 200 may pass through the objective lens 10. The secondary charged particle beam 140 may be influenced by the magnetic field 282.

The exemplary charged particle beam device 260 shown in FIG. 2b includes a stage 270, a sample voltage source 285, proxi electrodes 290 and a magnetic objective lens portion 280. Alternatively, according to embodiments described herein, the charged particle beam device may include any single one of these components or any subset of these components.

The working distance 120, the landing energy, the strength of the extraction field 292 and/or the strength of the magnetic field 282 are operating parameters of the secondary charged particle imaging system 200. The sample 125 may be inspected for different values of the operating parameters ranging across an operating window of the system 200. For example, in a first inspection round of the sample 125, the working distance 120, the landing energy, the extraction field strength and/or the strength of the magnetic field 282 may be set to a first configuration of values in the operating window. For a second inspection round of the sample 125, e.g. at a later moment in time compared to the first inspection round, the working distance 120, the landing energy, the extraction field strength and/or the strength of the magnetic field 282 may be set to a second configuration of values in the operating window. Inspecting the sample for different configurations of the operating parameters, as described above, may provide information about a variety of aspects relating to, e.g., the structure, topography and composition of the sample.

Where the working distance 120, the landing energy, the strength of the extraction field 292 and/or the strength of the magnetic field 282 are adjusted, the excitation of the first lens 222 and of the second lens 224 may be individually adjusted under the control of the controller 240 to control the trajectory and/or shape of the secondary charged particle beam. Accordingly, independent of the configuration of values to which the operating parameters are set, embodiments described herein provide a shaping of the secondary charged particle beam 140 by the lens system 220 so that the secondary charged particle beam 140 is mapped onto the aperture plate. Therein, in the topography detection mode, the first sub-beam 142 passes through the first opening 232 of the aperture plate 230 and is subsequently detected by the first detection element 252, and the second sub-beam 144 passes through the second opening 234 and is subsequently detected by the second detection element 254.

According to an embodiment, a secondary charged particle imaging system for imaging a secondary charged particle beam emanating from a sample by impingement of a primary charged particle beam is provided. The system includes a detector arrangement and adaptive secondary charged particle optics. The detector arrangement includes a first detection element for detecting a first secondary charged particle sub-beam of the secondary charged particle beam, such as e.g. first sub-beam 142 shown in FIG. 1a, in a topography detection mode. The detector arrangement further includes a second detection element for detecting a second secondary charged particle sub-beam of the secondary charged particle beam, such as e.g. second sub-beam 144, in the topography detection mode. The first detection element and the second detection element are separated from each other. The adaptive secondary charged particle optics includes an aperture plate, a lens system for mapping the secondary charged particle beam onto the aperture plate, and a controller. The aperture plate includes a first opening for letting the first secondary charged particle sub-beam pass through and a second opening for letting the second secondary charged particle sub-beam pass through. The lens system includes a first lens and a second lens. The controller is configured for controlling the excitation of the first lens and the excitation of the second lens. With respect to the propagation of the secondary charged particle beam, the aperture plate is arranged upstream of the detector arrangement, the first lens is arranged upstream of the aperture plate, and the second lens is arranged upstream of the first lens. The controller is configured to independently control the excitation of the first lens and of the second lens to map the secondary charged particle beam onto the aperture plate so that the first secondary charged particle sub-beam passes through the first opening and the second secondary charged particle sub-beam passes through the second opening in the topography detection mode independent of a variation of at least one first operating parameter. The at least one first operating parameter is selected from a group including: landing energy of the primary charged particle beam on the sample, extraction field strength for the secondary charged particle beam at the sample, magnetic field strength of an objective lens that focuses the primary charged particle beam onto the sample, and working distance of the objective lens from the sample.

Compared to a secondary charged particle imaging system including a single lens for focusing the secondary charged particle beam, the lens system described herein, including a first lens and a second lens, provides more degrees of freedom for shaping the secondary charged particle beam. Accordingly, the lens system described herein offers several advantages as discussed in the following.

Varying one or more operating parameters, e.g. one or more of the at least one first operating parameter, could in some systems lead to variations in the trajectory and/or the shape of the secondary charged particle beam, e.g. focal position variations and opening angle variations. Accordingly, the secondary charged particle beam could deviate from a target trajectory and/or target shape, which could lead to a poor image quality. The first lens and the second lens of the lens system, as provided by embodiments described herein, allow for mapping the secondary charged particle beam on the aperture plate in the topography detection mode (and in a bright field detection mode, as described herein) according to a target shape and trajectory independent of the variation of operating parameters across the operating window of the system. For example, embodiments described herein, providing a first lens and a second lens, allow for reducing or eliminating at least one of the following: an axial shift, along an optical axis defined by the aperture plate, of a cross-over position of the secondary charged particle beam entering the detector arrangement; a radial shift of the cross-over position of the secondary charged particle beam with respect to the plane perpendicular to the optical axis of the aperture plate; a variation of an opening angle of the secondary charged particle beam at the cross-over of the secondary charged particle beam; and a variation of a Larmor rotation of the secondary charged particle beam in response to a variation of the strength of a magnetic field generated by the objective lens.

Accordingly, a good image quality can be provided for all configurations of the operating parameters in the operation window. Compared to a system including a single lens for focusing the secondary charged particle beam, embodiments described herein provide a good image quality for a larger operating window. In particular, the set of configurations of operating parameters for which a good image quality can be provided by embodiments described herein is larger compared to systems including a single lens for focusing the secondary charged particle beam.

According to embodiments described herein, which can be combined with other embodiments described herein, the working distance may be within or may be varied within the range from 0.1 mm to 5 mm, more particularly from 0.2 mm to 3 mm, still more particularly from 0.5 to 2 mm, for example 1 mm. According to embodiments, which can be combined with other embodiments described herein, for a charged particle beam device where the secondary charged particles are electrons, the landing energy may be within or may be varied within the range from 0 to 20 keV, more particularly from 0.1 to 10 keV, still more particularly from 0.1 to 6 keV. The extraction field may be within or may be varied within the range from 0 to 5000 V/mm, more particularly from 0 to 4000 V/mm, still more particularly from 0 to 3000 V/mm.

Further advantages of embodiments described herein, providing a first lens and a second lens, are discussed with respect to FIGS. 3a-c and 4a-c. In the discussion of FIGS. 3a-c and 4a-c, the secondary charged particles are electrons.

FIG. 3a illustrates an example where an electron beam system 300 is operated in a topography detection mode at a landing energy of 6 keV and an extraction field of 3000 V/mm. As shown in FIG. 3a, a cross-over of the secondary charged particle beam 140 occurs at a cross-over position 312 inside the single lens 310. Accordingly, the single lens 310 may not be adapted for influencing an opening angle of the secondary charged particle beam 140 traveling away from the cross-over position 312. In contrast, using a lens system including a first lens and a second lens, as described herein, the opening angle may be adjusted and controlled. Even if the cross-over were to occur inside, e.g., the first lens of the lens system, the opening angle can be influenced, e.g. enlarged, by the second lens arranged at a distance from the first lens.

FIG. 3b illustrates an example where an electron beam system 300 is operated in a topography detection mode at a landing energy of 1 keV and an extraction field of 80 V/mm. As shown in FIG. 3b, the opening angle 316 of the secondary charged particle beam 140 upstream of the single lens 310 is large, such that the diameter of the secondary charged particle beam entering the single lens 310 is larger than the interior diameter 318 of the single lens 310. Accordingly, part of the secondary charged particle beam may not pass through the single lens 310 and, accordingly, get lost and be undetected. In contrast, using a lens system including a first lens and a second lens, as described herein, the secondary charged particle beam may be influenced by the first lens and by the second lens so that the entire secondary charged particle beam may pass through the lens system and reach the detector arrangement. For example, the first lens could be arranged at a position, e.g. to the left of the single lens 310 shown in FIG. 3b, where the diameter of the secondary charged particle beam is narrow.

FIG. 3c illustrates an example where an electron beam system 300 is operated in a topography detection mode at a landing energy of 0.1 keV and an extraction field of 1000 V/mm. As shown in FIG. 3c, the secondary charged particle beam 140 passing through the single lens 310 is narrow. Accordingly, even with a strong excitation of the single lens 310 and by providing an additional cross-over of the secondary charged particle beam 140, the opening angle of the secondary charged particle beam 140 might not be sufficiently large. Accordingly, only a weak detection signal may be provided. In contrast, using a lens system including a first lens and a second lens, as described herein, even a narrow secondary charged particle beam may be shaped by the first lens and by the second lens so that a strong detection signal is generated.

FIGS. 4a-c illustrate embodiments where a charged particle beam device including the lens system 220, including the first lens 222 and the second lens 224, is operated in the topography detection mode for different values of the landing energy and of the extraction field. FIG. 4a illustrates an embodiment where the charged particle beam device is operated at a landing energy of 6 keV and an extraction field of 3000 V/mm. FIG. 4b illustrates an embodiment where the charged particle beam device is operated at a landing energy of 6 keV and an extraction field of 80 V/mm. FIG. 4c illustrates an embodiment where the charged particle beam device is operated at a landing energy of 0.1 keV and an extraction field of 1000 V/mm. As shown, even though the embodiments illustrated in FIGS. 4a-c involve different configurations of the landing energy and the extraction field, the secondary charged particle beam 140 is mapped onto the aperture plate 230, wherein the first sub-beam 142 passes through the first opening 232, the second sub-beam 144 passes through the second opening 234 and the third sub-beam 546 passes through the central opening 520.

Figure 5:
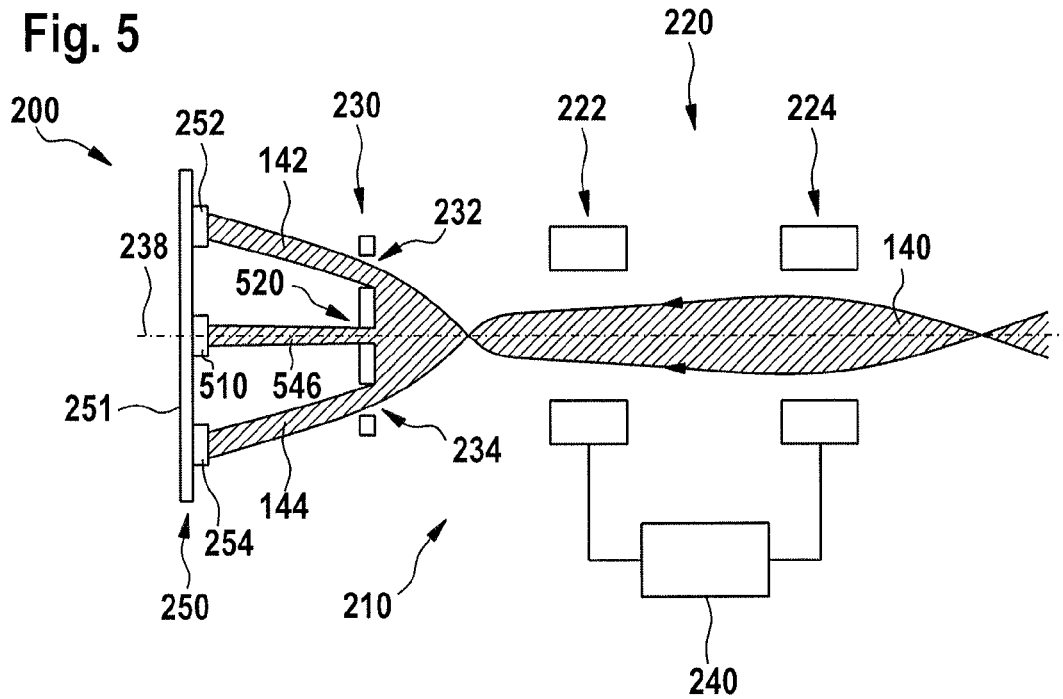
FIG. 5 shows a secondary charged particle imaging system according to embodiments described herein, in a state of operation according to a topography detection mode.
Figure 6:
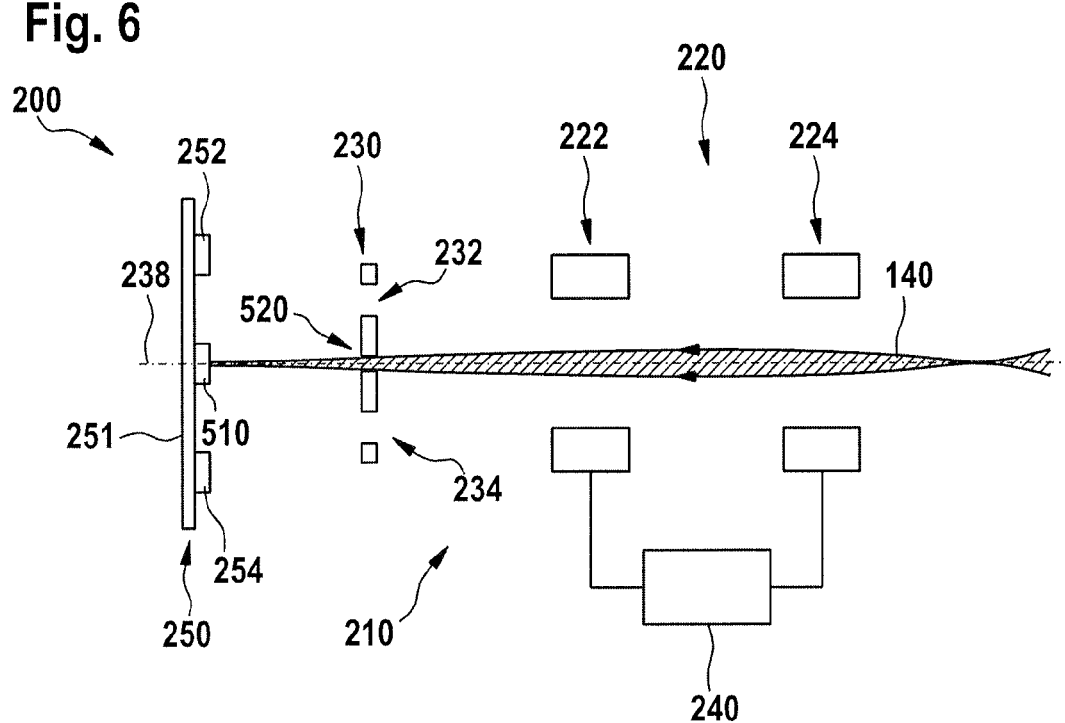
FIG. 6 shows a secondary charged particle imaging system according to embodiments described herein, in a state of operation according to a bright field detection mode.

FIGS. 5 and 6 show a secondary charged particle imaging system 200 according to embodiments described herein. The detector arrangement 250 shown in FIGS. 5 and 6 includes a central detection element 510. As shown, the central detection element 510 may be arranged between the first detection element 252 and the second detection element 254. The central detection element 510 may be fixed to the holder 251. The aperture plate 230 shown in FIGS. 5 and 6 includes a central opening 520. As shown, the central opening 520 may be formed between the first opening 232 and the second opening 234.

According to embodiments, which can be combined with other embodiments described herein, and as illustrated in FIG. 5, the aperture plate 230 may define an optical axis 238. The first lens 222 and the second lens 224 may be aligned to the optical axis 238 of the aperture plate. According to embodiments, which can be combined with other embodiments described herein, the optical axis 238 may pass through the central opening 520 of the aperture plate 230. The first opening 232 and/or the second opening 234 may be arranged radially outward from the optical axis 238.

According to embodiments, which can be combined with other embodiments described herein, the optical axis 238 may extend through the central detection element 510. The optical axis 238 may be perpendicular or substantially perpendicular to a plane defined by the aperture plate 230, to a plane defined by the holder 251, to a plane defined by the first lens 222/and or to a plane defined by the second lens 224. The terminology "substantially perpendicular" may refer to an angle between 90 and 110 degrees. The optical axis 238 may be a symmetry axis of the aperture plate 230, of the holder 251, of the first lens 222/and or of the second lens 224. According to embodiments, which can be combined with other embodiments described herein, the first detection element 252 and the second detection element 254 may be arranged radially outward from the optical axis 238. The secondary charged particle beam 140 traveling from the first lens 222 to the second lens 224 may substantially travel along the optical axis 238.

Similar to FIG. 2a, the secondary charged particle imaging system 200 shown in FIG. 5 is in a state of operation according to the topography detection mode. According to the embodiment illustrated in FIG. 5, the secondary charged particle beam 140 passes through the first opening 232, through the second opening 234 and through the central opening 520 of the aperture plate 230. As shown, a third sub-beam 546 of the secondary charged particle beam 140 may be formed at the central opening 520 of the aperture plate 230. The third sub-beam may consist of secondary charged particles which, upon approaching the aperture plate 230, travel along a path making a comparatively small angle with respect to the optical axis 238. The first sub-beam 142 and the second sub-beam 144 may consist of secondary charged particles which, upon approaching the aperture plate 230, travel along a path making a comparatively large angle with the optical axis 238.

In the topography detection mode, the third sub-beam 546 may pass through the central opening 520. The third sub-beam 546 may travel from the central opening 520 to the central detection element 510. The third sub-beam 546 may subsequently be detected by the central detection element 510 in the topography detection mode.

According to embodiments, which can be combined with embodiments described herein, the controller 240 may be configured to independently control the excitation of the first lens 222 and of the second lens 224 to map the secondary charged particle beam 140 onto the aperture plate 230 so that a third secondary charged particle sub-beam, such as e.g. the third sub-beam 546, of the secondary charged particle beam 140 may pass through the central opening 520 in the topography detection mode. By individually adjusting the excitation of the first lens 222 and of the second lens 224 under the control of the controller 240, the first sub-beam 142, the second sub-beam 144 and the third sub-beam 546 may pass through the first opening 232, the second opening 234 and the central opening 520, respectively, independent of a variation of the at least one operating parameter as described herein.

The secondary charged particle imaging system 200 shown in FIG. 6 is in a state of operation according to a bright field detection mode. As illustrated in FIG. 6, in the bright field detection mode, the secondary charged particle beam 140 may pass entirely through the central opening 520. As further shown in FIG. 6, in the bright field detection mode, the secondary charged particle beam 140 may travel from the central opening 520 to the central detection element 510. Therein, the secondary charged particle beam may travel substantially along the optical axis 238. The secondary charged particle beam 140 may subsequently be detected entirely by the central detection element 510 in the bright field detection mode. In the bright field detection mode, the first detection element 252 and the second detection element 254 may not be utilized for detecting the secondary charged particle beam 140.

In the bright field detection mode, the deceleration field at the aperture plate 230 may be switched off. Alternatively, a deceleration field may be applied in the bright field detection mode. The deceleration field may provide an energy filter. According to some embodiments, when an energy filter is applied, the secondary charged particles may be focused into a center of the central opening 520 of the aperture plate 230 in the bright field detection mode.

According to embodiments, which can be combined with other embodiments described herein, the controller 240 may be configured to independently control the excitation of the first lens 222 and of the second lens 224 to map the secondary charged particle beam 140 onto the aperture plate 230 so that the secondary charged particle beam 140 passes entirely through the central opening 520 in the bright-field detection mode independent of a variation of at least one second operating parameter. The at least one second operating parameter may be selected from a group including: landing energy of the primary charged particle beam on the sample, extraction field strength for the secondary charged particle beam at the sample, magnetic field strength of an objective lens that focuses the primary charged particle beam onto the sample, and working distance of the objective lens from the sample, as illustrated in FIG. 2b. According to embodiments, which can be combined with other embodiments described herein, the at least one first operating parameter is the same as the at least one second operating parameter.

Figure 7A:
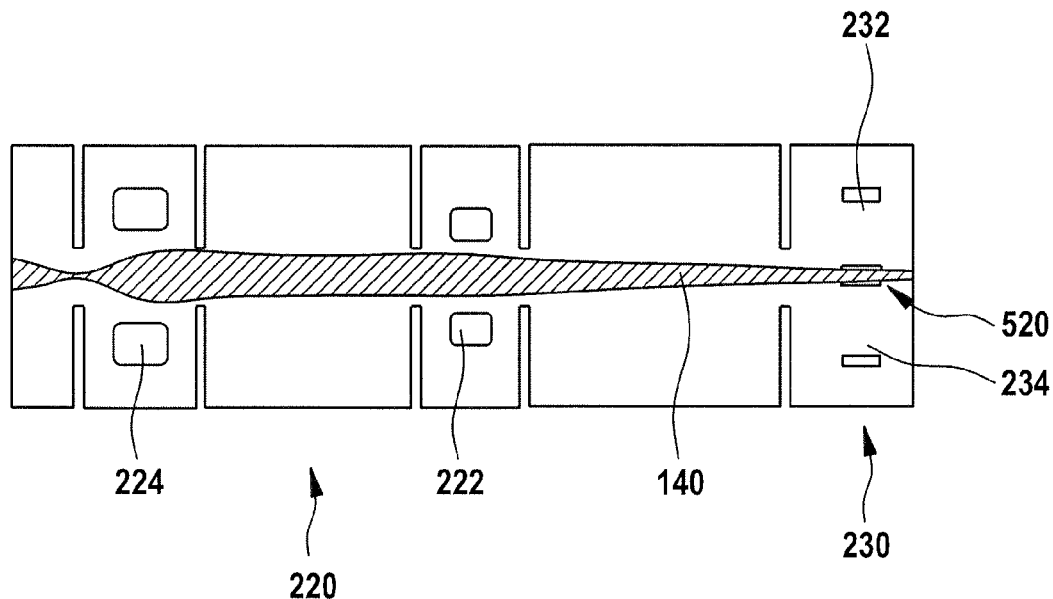
FIGS. 7a-b illustrate embodiments where a charged particle beam device, according to embodiments described herein, is operated in a bright field detection mode for different values of the landing energy and of the extraction field strength.
Figure 7B:
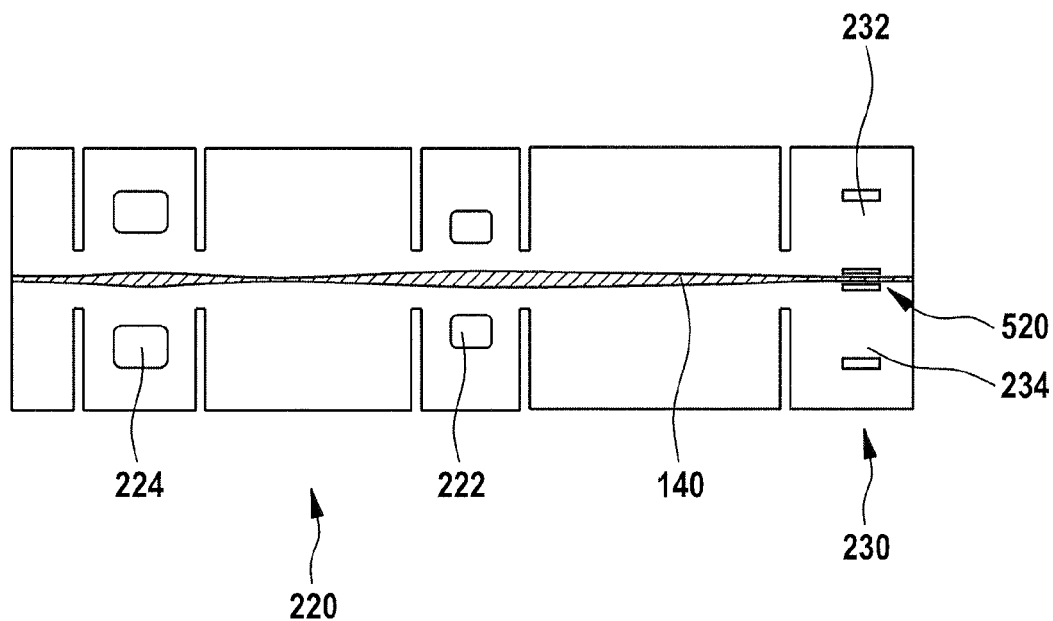

FIGS. 7a-b illustrate embodiments where a charged particle beam device providing the first lens 222 and the second lens 224 is operated according to the bright field detection mode for different values of the landing energy and of the extraction field. FIG. 7a illustrates an embodiment where the charged particle beam device is operated at a landing energy of 1 keV and an extraction field of 0 V/mm. FIG. 7b illustrates an embodiment where the charged particle beam device is operated at a landing energy of 1 keV and an extraction field of 3000 V/mm. As shown, according to each of the embodiments illustrated in FIGS. 7a-b, the secondary charged particle beam 140 is mapped onto the aperture plate 230, wherein the secondary charged particle beam 140 passes entirely through the central opening 520.

According to embodiments, which can be combined with other embodiments described herein, the controller 240 may be configured to switch between the topography detection mode and the bright-field detection mode by adapting the excitations of the first lens 222 and of the second lens 224. At a first moment in time, the excitations of the first lens 222 and of the second lens 224 may be set to a first configuration under the control of the controller 240 to image the secondary charged particle beam 140 in the topography detection mode. At a second, e.g. later, moment in time, the excitations of the first lens 222 and of the second lens 224 may be set to a second configuration under the control of the controller 240 to image the secondary charged particle beam 140 in the bright field detection mode. Accordingly, the flexibility of the system is enhanced.

An advantage of having a controller configured for switching between the topography detection mode and the bright field detection mode, compared to a system configured for operating solely according to either topography detection mode or according to the bright field detection mode, is that multiple aspects of the sample, relating to e.g. topography information, defects on the sample, chemical constituents of the sample, and the like, can be analyzed by a single system.

Figure 8A:
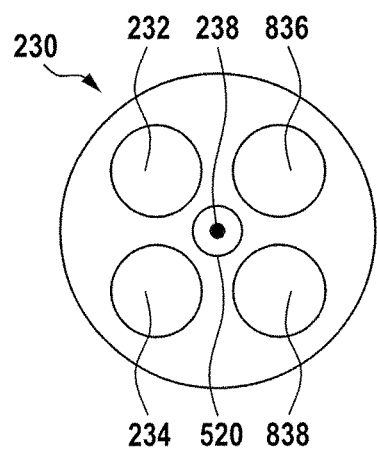
FIG. 8a shows an aperture plate of a secondary charged particle imaging system according to embodiments described herein.

FIG. 8a shows a front view of the aperture plate 230 of the secondary charged particle imaging system according to embodiments described herein. In addition to the first opening 232, the second opening 234 and the central opening 520, the aperture plate 230 may include further openings, such as two further openings 836 and 838 as shown in FIG. 8a. The aperture plate 230 shown in FIG. 8a includes five openings 232, 234, 520, 836 and 838. The first opening 232, the second opening 234 and the further openings 836 and 838 are located around the optical axis 238 such that the aperture plate 230 has a four-fold rotational symmetry with respect to the optical axis 238. The first opening 232, the second opening 234 and the further openings 836 and 838 are radially outward openings with respect to the optical axis 238. The diameter or the corresponding dimension of the central opening 520 may be 1 mm to 4 mm. For the first opening 232, the second opening 234 and/or the further openings 836 and 838, the diameter or a corresponding dimension can be 3 mm to 15 mm. The distance between the center of the first opening and the center of the second opening may be in the range from 4 to 15 mm.

Figure 8B:
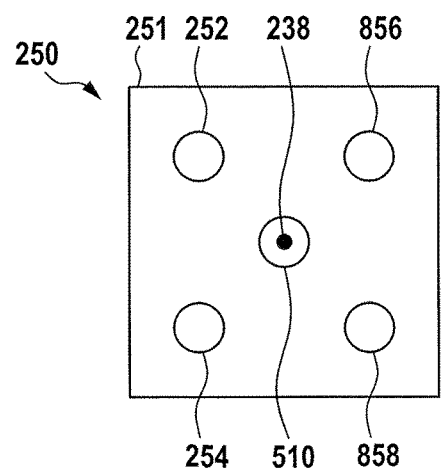
FIG. 8b shows a detector arrangement of a secondary charged particle imaging system according to embodiments described herein.

FIG. 8b shows a front view of the detector arrangement 250 of a secondary charged particle imaging system according to embodiments described herein. In addition to the first detection element 252, the second detection element 254 and the central detection element 510, the detector arrangement 250 may include further detection elements, such as two further detection elements 856 and 858 as shown in FIG. 8b. The detector arrangement 250 shown in FIG. 8b includes five detection elements 252, 254, 510, 856 and 858, i.e. the same number of detection elements as the number of openings provided in the aperture plate 230 shown in FIG. 8a. Each of the five detection elements shown in FIG. 8b is associated with one corresponding opening in the aperture plate 230 shown in FIG. 8a. According to embodiments, which can be combined with other embodiments described herein, the detector arrangement 250 includes an integer number N of further detection elements, the integer number N either being zero or being larger than zero. The aperture plate 230 may comprise the same integer number N of further openings, wherein the first opening 232, the second opening 234 and the N further openings are located around the optical axis 238 of the aperture plate 230 such that the aperture plate 230 has an N+2-fold rotational symmetry with respect to the optical axis 238 of the aperture plate 230.

A detection element of the detector arrangement 250, such as e.g. the first detection element 252, the second detection element 254 and/or the central detection element 510, may e.g. be a pin diode detector or a scintillator detector. Particularly for EBI applications, high throughput is desired, which results in the need for very fast sensors. Accordingly, pin diode detectors can be used. The obtainable bandwidth may depend on the size of the pin diode detector. A sensor area of 1 mm² or below may be utilized.

The first detection element 252, the second detection element 254, the central detection element 510 and/or further detection elements of the detector arrangement 250 may be individual detectors which may be spatially separated from each other. The individual signals obtained by the detection elements of the detector arrangement can be combined (e.g. subtracted) to enhance contrast. Compared to e.g. detection elements which are arranged proximate to each other, e.g. segmented pin diodes, having spatially separated detection elements provides the advantage that problems relating to a pin diode area which separates active segments (e.g. charging, signal loss, cross-talk) can be more easily overcome. Further, spatially separated detection elements are less expensive, have a shorter development cycle, an improved flexibility in sensor design and a faster time-to-market.

The distance between the first detection element and the second detection element may be in the range from 1 to 20 mm. The distance between the first detection element and the central detection element may be in the range from 1 to 14 mm.

Compared to e.g. a bright field detector, the detector arrangement 250 including multiple detection elements, as described herein, provides an enhanced sensitivity to changes in the topography of the sample, e.g. resulting from physical defects. The multiple detection elements may collect only secondary charged particles within certain ranges of take-off angles at the sample. Accordingly, an enhanced contrast of the inspected features and/or defects, e.g. for defect inspection tools and review tools or critical dimensioning tools, may be provided.

The detector arrangement 250 may be an integrated detector arrangement. The first detection element 252, the second detection element 254 and/or the central detection element 510 may be integrated into the detector arrangement. The detection elements of the detector arrangement 250 may be separated from each other in the integrated detector arrangement. The detection elements of the detector arrangement 250 may be fixedly positioned in or at the detector arrangement 250. The detection elements of the detector arrangement 250 may be fixed onto a holder or holder plate of the detector arrangement 250.

Figure 9:
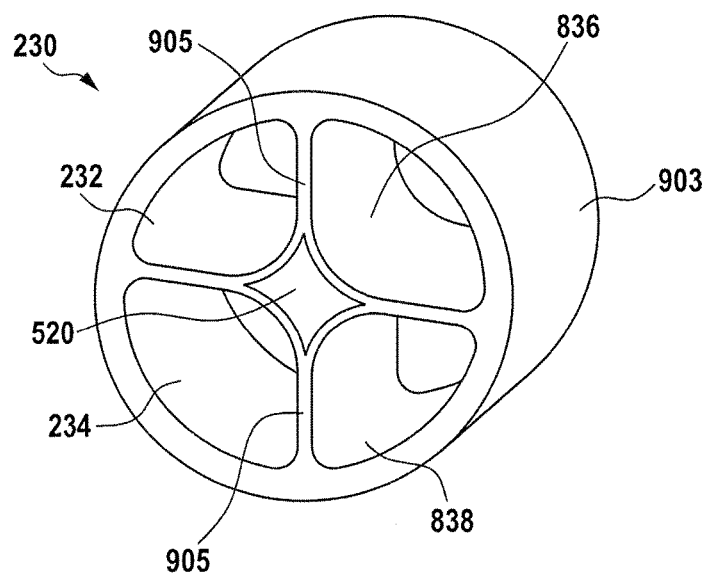
FIG. 9 shows an aperture plate of a secondary charged particle imaging system according to embodiments described herein.

As illustrated in FIG. 9, the aperture plate 230 may have an outer portion 903, e.g. a circular body. The area between the first opening 232, the second opening 234, the central opening 520 and the further openings 836 and 838 is provided by division bars 905. Accordingly, the area between the openings is reduced to be narrower when compared to, e.g., the aperture plate 230 shown in FIG. 8a. In the aperture plate 230 shown in FIG. 9, the central opening 520 is provided, e.g. with a pincushion shape. The central opening 520 shown in FIG. 9 has concave portions, i.e. portions that are bended inwardly towards the center of the opening. The central opening 520 shown in FIG. 9 has at least four concave regions in the perimeter. Accordingly, the potential distribution in outer openings, e.g. the first opening 232, the second opening 234 and the further openings 836 and 838, can be smoothened, which leads to better focusing properties, particular of the outer openings. As further shown in FIG. 9, the outer openings may be defined at least at two sides by a bar, e.g. a division bar 905. Accordingly, the outer openings have a straight boundary at a length of at least 30% of their perimeter.

In light of the above, it is possible to provide a reduction of the loss of secondary charged particles at the aperture plate from typically about 30% to less than 5%. The loss of secondary charged particles is inter alia achieved by reducing the head-on cross-section of the device. That is, embodiments described herein have a reduced area with solid material in the cross-section.

The aperture plate may have a thickness of 5 mm or above, more particularly the thickness may be from 10 mm to 20 mm. The thickness of the aperture plate may be a thickness in an axial direction of the aperture plate and/or in a direction parallel to the optical axis defined by the aperture plate. Having a thickness from 10 mm to 20 mm may provide an increased separation of the sub-beams of the secondary charged particle beam. The increased separation allows for the utilization of a detector arrangement where the detection elements, e.g. the first detection element, the second detection element and/or the central detection element, may be standard pin diodes with a 5 mm diameter. Accordingly, a feasible design of the detector arrangement may be provided. Further, in light of the fact that the reach-through of an acceleration field generated between the aperture plate and the detector arrangement is influenced by the thickness of the aperture plate, a reduced operating voltage is a beneficial side effect from having a minimum thickness of the aperture plate of at least 5 mm. Accordingly, better high voltage immunity, reliability and stability may be provided.

Figure 10:
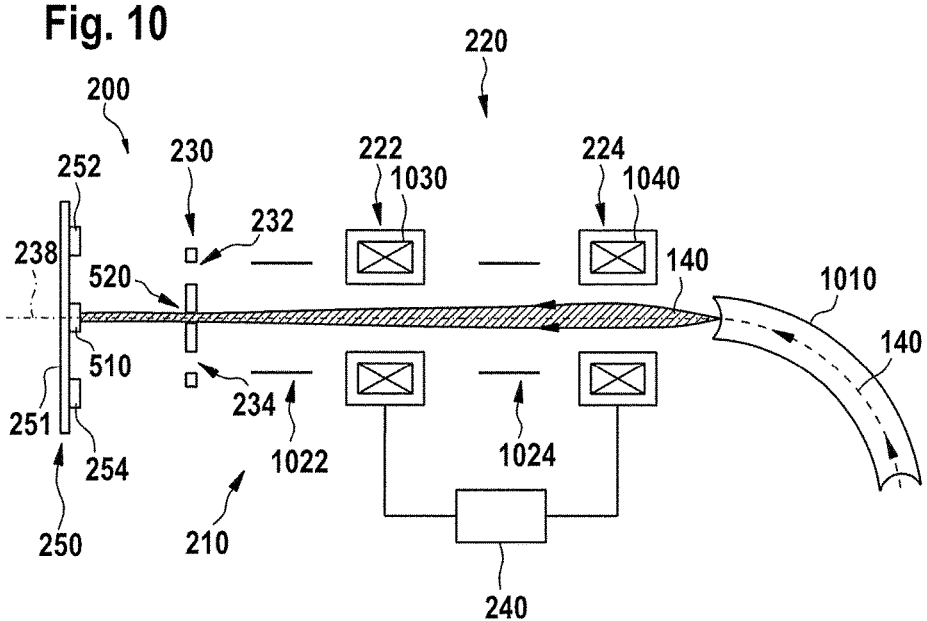
FIG. 10 shows a secondary charged particle imaging system according to embodiments described herein.

FIG. 10 shows a secondary charged particle imaging system 200 according to embodiments described herein. The secondary charged particle imaging system 200 includes a beam bender 1010 for bending the secondary charged particle beam 140. A beam bender may e.g. be a hemispherical sector. A beam bender may be adapted for changing the direction of the secondary charged particle beam, so that the travel direction of the secondary charged particle beam entering the beam bender is different when compared to the travel direction of the secondary charged particle beam leaving the beam bender. The beam bender may be arranged to direct the secondary charged particle beam further away from a primary charged particle beam.

According to embodiments, which can be combined with other embodiments described herein, the beam bender 1010 acting on the secondary charged particle beam 140 is arranged, with respect to the secondary charged particle beam 140, upstream of the second lens 224. In the drawing plane of FIG. 10, the beam bender 1010 is arranged to the right of the second lens 224. As shown, the secondary charged particle beam 140 enters the beam bender 1010 from below and travels through the beam bender 1010. The secondary charged particle beam 140 exiting the beam bender travels along a substantially horizontal direction. The secondary charged particle beam 140 travels from the beam bender 1010 to the second lens 224 of the lens system 220. As illustrated in FIG. 10, the second lens 224 may be arranged, with respect to the secondary charged particle beam 140, directly downstream of the beam bender 1010. The second lens 224 may be the next element acting on the secondary charged particle beam 140 leaving the beam bender 1010. An opening angle of the secondary charged particle beam, as described herein, may be an opening angle of the secondary charged particle beam exiting the beam bender 1010.

It is considered beneficial to arrange the second lens 224 as close as possible to the beam bender 1010 and to arrange the first lens 222 sufficiently far away from the beam bender 1010. According to embodiments, which can be combined with other embodiments described herein, the distance between the beam bender 1010 and the second lens 224 is 60 mm or below, in particular 45 mm or below, more particularly from 20 mm to 35 mm. According to embodiments, which can be combined with other embodiments described herein, the distance between the beam bender 1010 and the first lens 222 is 50 mm or above, more particularly 100 mm or above, for example from 115 mm to 180 mm.

As further shown in FIG. 10, the secondary charged particle imaging system 200 may include one or more deflection elements for influencing the secondary charged particle beam 140. By providing one or more deflection elements, the information carried by the secondary charged particles is more easily conserved as the secondary charged particle beam 140 is transferred from the sample to the detector arrangement 250. As shown, a first deflection element 1022 and a second deflection element 1024 may be arranged between the beam bender 1010 and the detector arrangement 250. According to alternative embodiments, the secondary charged particle imaging system 200 may include the first deflection element 1022 without the second deflection element 1024 or vice versa, or may include additional deflection elements arranged between the beam bender 1010 and the detector arrangement 250. A third deflection element (not shown) may be provided between the beam bender 1010 and the second lens 224. Alternatively, a third deflection element may be provided upstream, with respect to the secondary charged particle beam 140, of the beam bender 1010. For example, a third deflection element may be provided between a beam separator, as described herein, and the beam bender. A third deflection element improves alignment and/or imaging of the secondary charged particle beam on the detector arrangement. Accordingly, signal generation, and thus contrast, can be improved. The improved signal generation results in better throughput, particularly for EBI applications. The third deflection element may be the next deflection element through which the secondary charged particle beam 140 leaving the beam bender 1010 passes. The third deflection element may be arranged directly downstream, with respect to the secondary charged particle beam 140, of the beam bender 1010. Alternatively, the third deflection element may be provided between the first lens 222 and the detector arrangement 250. Providing the third deflection element between the beam bender and the second lens or between the first lens and the detector arrangement, as described above, has the advantage that a potential space restriction for a third deflection element is not as critical as compared to e.g. a third deflection element being positioned between a beam separator and the beam bender (insufficient separation between secondary charged particle beam and primary charged particle beam). Arranging the third deflection element between a beam separator and the beam bender may provide an improved anti-scanning of the secondary charged particle beam. In particular, deviations of the secondary charged particle beam emanating from an off-axial position with respect to the axis of a secondary charged particle beam starting in the center of the field of view may be more easily compensated for.

As shown in FIG. 10, the second deflection element 1024 may be arranged between the first lens 222 and the second lens 224. The second deflection element 1024 may influence the secondary charged particle beam 140 traveling from the second lens 224 to the first lens 222. The first deflection element 1022 may be arranged between the aperture plate 230 and the first lens 222. The first deflection element 1022 may influence the secondary charged particle beam 140 traveling from the first lens 222 to the aperture plate 230. The first deflection element 1022 and/or the second deflection element 1024 may be aligned to the optical axis 238, as illustrated in FIG. 10. The optical axis 238 may extend longitudinally through the first deflection element 1022 and/or through the second deflection element 1024.

A deflection element for influencing the secondary charged particle beam, such as e.g. the first deflection element 1022 and/or the second deflection element 1024 shown in FIG. 10, may include an electrostatic deflection portion and/or a magnetic deflection portion. An electrostatic deflection portion may include an electrostatic dipole, quadrupole or higher order multi-pole element. A magnetic deflection portion may include a magnetic dipole, quadrupole or higher order multi-pole element. A deflection element may include two deflection plates arranged on opposite sides of the optical axis defined by the aperture plate and/or arranged on opposite sides of the secondary charged particle beam. For deflection in two directions, two perpendicular dipole fields may be provided or two deflectors may be provided that may be operated to allow for one dipole field, which can be rotated depending on the operation of the two deflectors. For example, individual fields of the two deflectors separately can enclose an angle of 70° to 110°, such as 90°. As shown in FIG. 10, the first deflection element 1022 and/or the second deflection element 1024 may each include two deflection plates for deflecting the secondary charged particle beam in a first direction.

A deflection element for influencing the secondary charged particle beam may be adapted to align the secondary charged particle beam with the optical axis of the aperture plate, e.g. in the bright field detection mode. Additionally or alternatively, a deflection element, e.g. a third deflection element as described herein, may be adapted for anti-scanning the secondary charged particle beam. The secondary charged particle beam may be anti-scanned in a charged particle beam device where the primary charged particle beam is scanned over a sample. Scanning the primary charged particle beam over the sample may provide an unwanted deflection of the secondary charged particle beam, wherein the position of the secondary charged particle beam impinging onto the detector arrangement and/or the position of the secondary charged particle beam with respect to the aperture plate may depend on the primary charged particle beam position being scanned over the sample. This dependence may lead to a poor detection quality and a blurred image. Anti-scanning of the secondary charged particle beam, e.g. by the first deflection element 1022 and/or by the second deflection element 1024 shown in FIG. 10, may compensate for the deflection of the secondary charged particle beam resulting from scanning the primary charged particle beam and/or may align the secondary charged particle beam with a target axis, e.g. the optical axis defined by the aperture plate, independent of the position of the primary charged particle beam being scanned over the sample. Accordingly, off-axis aberrations of the secondary charged particle beam may be avoided. Anti-scanning of the secondary charged particle beam may be particularly beneficial for a charged particle beam device having a large field of view. According to embodiments, which can be combined with other embodiments described herein, the field of view of the charged particle beam device may be 500 μm or above.

To provide an anti-scanning of the secondary charged particle beam with a deflection element, a deflection voltage may be applied to the deflection element. The deflection voltage may be synchronized with the scanning of the primary charged particle beam to compensate a deflection of the secondary charged particle beam resulting from the scanning of the primary charged particle beam.

A deflection element configured for anti-scanning the secondary charged particle beam may be arranged, with respect to the secondary charged particle beam, upstream of the aperture plate, upstream of the first lens and/or between the first lens and the second lens. Compared to anti-scanning the secondary charged particle beam downstream of the aperture plate, anti-scanning upstream of the aperture plate has the advantage that the secondary charged particle beam can be more easily aligned with a target axis. Further, anti-scanning upstream of the aperture plate may be advantageous for systems where an energy filter is provided at the aperture plate, as the energy filter has an increased sensitivity to the position of the secondary charged particle beam with respect to the optical axis 238.

As further shown in FIG. 10, the first lens 222 may include a first magnetic lens portion 1030 adapted for generating a magnetic field. The first magnetic lens portion 1030 may include a coil for generating the magnetic field.

The first magnetic lens portion 1030 may have an iron cladding. Similarly, the second lens 224 may include a second magnetic lens portion 1040. The second magnetic lens portion 1040 may include similar components compared to the first magnetic lens portion 1030. The first magnetic lens portion 1030 and/or the second magnetic lens portion 1040 may be adapted for compensating a Larmor rotation of the secondary charged particle beam 140. The Larmor rotation may be introduced in the secondary charged particle beam 140 due to a variation of the strength of a magnetic field generated by the objective lens of the charged particle beam device, e.g., the magnetic field 282 shown in FIG. 2b. The first magnetic lens portion 1030 and/or the second magnetic lens portion 1040 may be adapted for rotating the secondary charged particle beam 140. The rotation of the secondary charged particle beam 140 may be a rotation around the optical axis 238 defined by the aperture plate 230 and may be a clock-wise or a counter-clockwise rotation. The first magnetic lens portion 1030 may be adapted for rotating the secondary charged particle beam 140 by a first angle $A_1$. The first angle $A_1$ may lie in the range from −45 to 45 degrees. Accordingly, a Larmor rotation from −45 to 45 degrees can be compensated by the first magnetic lens portion. The second magnetic lens portion 1040 may be adapted for rotating the secondary charged particle beam 140 by a second angle $A_2$. The second angle $A_2$ may lie in the range from −45 to 45 degrees. Accordingly, a Larmor rotation from −45 to 45 degrees can be compensated for by the second magnetic lens portion. A lens system where the first lens includes a first magnetic lens portion and the second lens includes a second magnetic lens portion, such as e.g. the lens system 220 shown in FIG. 10, may be adapted for rotating the secondary charged particle beam by a total angle lying in the range from $-|A_1|-|A_2|$ to $|A_1|+|A_2|$ where $|A_1|$ and $|A_2|$ denote the absolute values of $A_1$ and $A_2$, respectively. Accordingly, a Larmor rotation lying in the range from $-|A_1|-|A_2|$ to $|A_1|+|A_2|$ can be compensated for by the lens system. For example, a Larmor rotation between −90 and 90 degrees can be compensated for.

An advantage of compensating the Larmor rotation of the secondary charged particle beam with a first magnetic lens portion included in the first lens and/or a second magnetic lens portion included in the second lens is that no mechanical rotation of the aperture plate and/or the detector arrangement for compensating the Larmor rotation is required.

According to the exemplary embodiment illustrated in FIG. 10, the first lens 222 is a compound lens including an electrostatic lens portion (not shown) and a first magnetic lens portion 1030. Compared to a first lens including an electrostatic lens portion but no first magnetic lens portion, a compound lens provides additional degrees of freedom for influencing the secondary charged particle beam. In particular, two such additional degrees of freedom provided by a first magnetic lens portion 1030 may include the magnitude and direction of a current passed through a coil included in the first magnetic lens portion 1030. Similar considerations apply to embodiments where the second lens is a compound lens.

The magnetic field generated by the first magnetic lens portion 1030 may affect the focusing of the secondary charged particle beam 140 onto the aperture plate 230. Such a focusing effect may be compensated for or further enlarged by setting the excitation of the electrostatic lens portion of the first lens 222 to an appropriate value. For example, the focusing effect may be affected by reducing or increasing the refractive power of the electrostatic lens portion. Accordingly, the secondary charged particle beam 140 may be shaped, focused and/or defocused in a desired manner. Accordingly, via a combined action of the first magnetic lens portion 1030 and the electrostatic lens portion, the first lens 222 may allow for both compensating a Larmor rotation of the objective lens and for shaping, focusing and/or defocusing the secondary charged particle beam 140. Similar considerations apply to embodiments where the second lens is a compound lens.

Whereas according to the embodiment illustrated in FIG. 10 both the first lens 222 and the second lens 224 include a magnetic lens portion, according to other embodiments described herein only one of the first lens 222 and the second lens 224 may include a magnetic lens portion for compensating the Larmor rotation. According to embodiments, which can be combined with other embodiments described herein, at least one of the first lens and second lens comprises a magnetic lens portion for compensating the Larmor rotation of the objective lens. The controller may be configured to control, determine and/or adjust the excitation of the magnetic lens portion to map the secondary charged particle beam onto the aperture plate so that the first secondary charged particle sub-beam passes through the first opening and the second secondary charged particle sub-beam passes through the second opening in the topography detection mode independent of a variation in the magnetic field strength of the objective lens.

The exemplary secondary charged particle imaging system 200 shown in FIG. 10 includes a beam bender 1010, a first deflection element 1022, a second deflection element 1024, a first magnetic lens portion 1030 and a second magnetic lens portion 1040. Alternatively, according to embodiments described herein, the secondary charged particle imaging system may include any single one of these components or any combination of these components.

According to a further embodiment, a secondary charged particle imaging system for imaging a secondary charged particle beam emanating from a sample by impingement of a primary charged particle beam is provided. The secondary charged particle imaging system includes a detector arrangement, as described herein. The secondary charged particle imaging system further includes an adaptive secondary charged particle optics. The adaptive secondary charged particle optics includes an aperture plate, as described herein. The adaptive secondary charged particle optics further includes a lens system for mapping the secondary charged particle beam onto the aperture plate. The lens system includes a first lens, wherein the first lens includes a magnetic lens portion for compensating the Larmor rotation of an objective lens that focuses the primary charged particle beam onto the sample. The adaptive secondary charged particle optics further includes a controller for controlling the excitation of the first lens. With respect to the propagation of the secondary charged particle beam, the aperture plate is arranged upstream of the detector arrangement, and the first lens is arranged upstream of the aperture plate. The controller is configured to control the excitation of the first lens, including controlling the excitation of the magnetic lens portion, to map the secondary charged particle beam onto the aperture plate so that the first secondary charged particle sub-beam passes through the first opening and the second secondary charged particle sub-beam passes through the second opening in the topography detection mode independent of a variation in a magnetic field strength of the objective lens.

Figure 11:
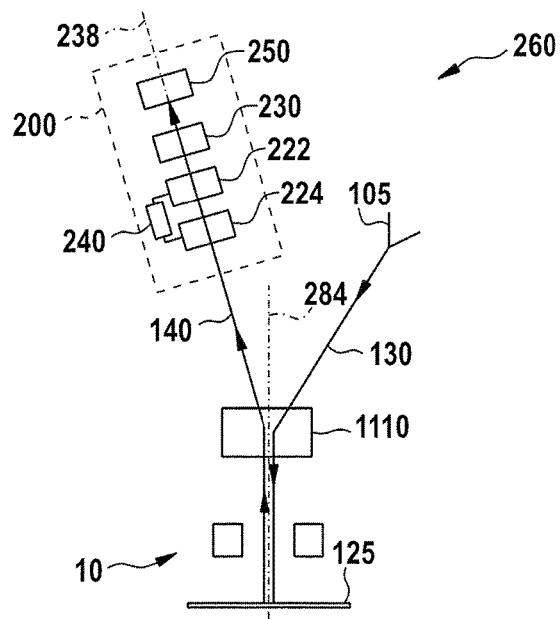
FIGS. 11 and 12 show a charged particle beam device according to embodiments described herein.
Figure 12:
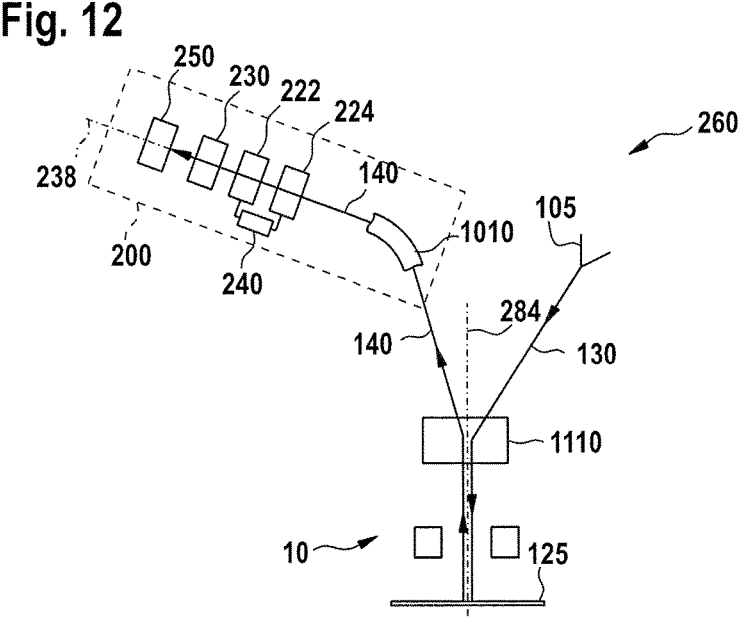

According to a further embodiment, and as illustrated in FIGS. 11-12, a charged particle beam device 260 is provided. The charged particle beam device 260 includes a beam emitter 105 for emitting a primary charged particle beam 130. The beam emitter 105 may e.g. be an electron gun. The charged particle beam device further includes an objective lens 10 for focusing the primary charged particle beam 130 onto a sample 125. The charged particle beam device 260 further includes a beam separator 1110 for separating the primary charged particle beam 130 from a secondary charged particle beam 140 emanating from the sample 125. The charged particle beam device 260 further includes a secondary charged particle imaging system 200 according to embodiments described herein. With respect to the propagation of the secondary charged particle beam 140, the secondary charged particle imaging system 200 may be arranged downstream of the beam separator 1110.

As shown in FIG. 11, the primary charged particle beam 130 emitted from the beam emitter 105 may travel from the beam emitter 105 to the beam separator 1110. As further shown, the primary charged particle beam 130 may be deflected in the beam separator 1110. As further shown, the primary charged particle beam 130 may travel from the beam separator 1110 to the objective lens 10 adapted for focusing the primary charged particle beam 130 onto the sample 125. According to the exemplary embodiment illustrated in FIG. 11, the primary charged particle beam 130, when traveling from the beam separator 1110 to the sample 125 via the objective lens 10, travels along the optical axis 284 defined by the objective lens 10. Upon impingement of the primary charged particle beam 130 on the sample 125, the secondary charged particle beam 140 is generated. As shown in FIG. 11, the secondary charged particle beam 140 may travel from the sample 125 to the beam separator 1110, wherein the secondary charged particle beam 140 may travel in the opposite direction of the primary charged particle beam 130. The beam separator 1110 acts on the primary charged particle beam 130 and on the secondary charged particle beam 140 and is adapted for separating the primary charged particle beam 130 from the secondary charged particle beam 140. As shown, the secondary charged particle beam 140 may be deflected in the beam separator 1110. The deflection may be such that the secondary charged particle beam leaving the beam separator is directed away from the primary charged particle beam 130. The secondary charged particle beam 140 travels from the beam separator 1110 to the secondary charged particle imaging system 200.

The beam separator 1110 may include a magnetic beam separation portion, e.g. including one or more coils, adapted for generating a magnetic field. Additionally or alternatively, the beam separator 1110 may include an electrostatic beam separation portion, e.g. including one or more electrodes, adapted for generating an electric field. The electric field and/or magnetic field may act on the primary charged particle beam 130 and on the secondary charged particle beam 140 passing through the beam separator 1110. Under the influence of the magnetic field and/or of the electric field, the primary charged particle beam 130 and/or the secondary charged particle beam may be deflected in the beam separator 1110.

As described above, e.g. in reference to FIG. 2b, the charged particle beam device 260 may further include at least one of the following: a stage 270, wherein the stage may be movable with respect to the objective lens 10 for varying the working distance 120; a sample voltage source 285 adapted for varying the landing energy of the primary charged particle beam 130; one or more proxi electrodes 290 adapted for varying the strength of the extraction field 292 acting on the secondary charged particle beam 140; a magnetic objective lens portion 280 included in the objective lens 10 adapted for generating a magnetic field 282. As further described above, under the action of the controller 240, the secondary charged particle beam 140 may be mapped onto the aperture plate 230, e.g. in the topography detection mode or in the bright field detection mode, independent of a variation of the at least one first operating parameter and/or independent of a variation of the at least one second operating parameter.

FIG. 12 shows a charged particle beam device 260 according to embodiments described herein. As was the case in FIG. 11, the charged particle beam device 260 shown in FIG. 12 includes the secondary charged particle imaging system 200 according to embodiments described herein. The secondary charged particle imaging system 200 shown in FIG. 12 includes the beam bender 1010, as discussed above. As further discussed above, the secondary charged particle beam 140 is directed away from the primary charged particle beam 130 by the beam separator 1110. The beam bender may direct the secondary charged particle beam 140 further away from the primary charged particle beam 130, as illustrated in FIG. 12.

Figure 13A:
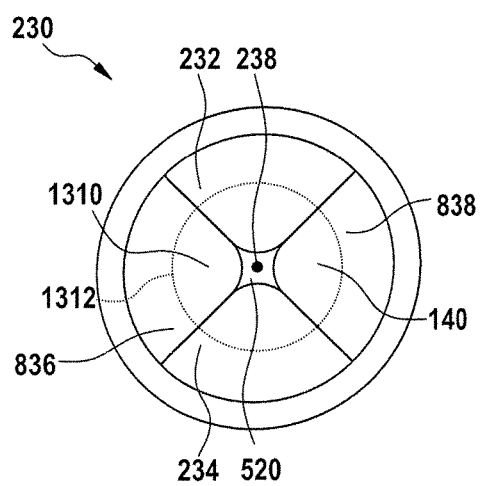
FIGS. 13a-b show an aperture plate of a secondary charged particle imaging system according to embodiments described herein.
Figure 13B:
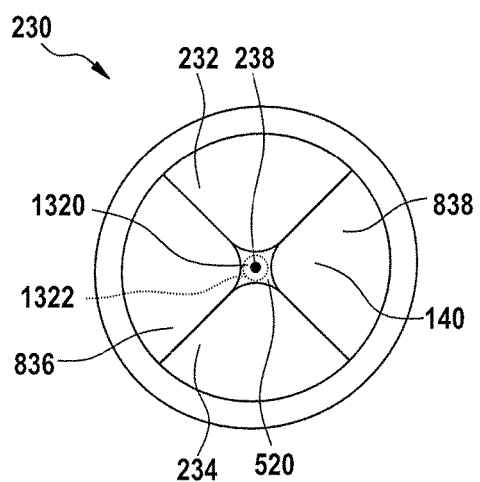

FIGS. 13a-b show a front view of the aperture plate of a secondary charged particle imaging system according to embodiments described herein. FIG. 13a shows the secondary charged particle beam 140 passing through the aperture plate 230 in the topography detection mode. In the topography detection mode, the secondary charged particle beam 140 is mapped onto a first region 1310 of the aperture plate 230 independent of a variation of the at least one first operating parameter. The first region may correspond to the cross-section, with respect to the drawing plane, of the secondary charged particle beam passing through the aperture plate 230 in the topography detection mode, independent of the variation of the at least one first operating parameter.

The exemplary first region 1310 shown in FIG. 13a has the shape of a disc. As shown, the first region 1310 has a boundary 1312 which, for the exemplary first region 1310 shown in FIG. 13a, is a circular boundary. Accordingly, the first region 1310 shown in FIG. 13a may correspond to a disc-shaped cross-section, with respect to the drawing plane, of the secondary charged particle beam 140 passing through the aperture plate 230 in the topography detection mode, independent of a variation of the at least one first operating parameter. As further shown in FIG. 13a, the first region 1310 may overlap with the first opening 232, the second opening 234 and/or the further openings 836 and 838. The cross-section of the central opening 520 with respect to the drawing plane may be contained in the first region 1310. As further shown in FIG. 13a, the optical axis 238 may extend through a center of the first region 1310.

According to embodiments, which can be combined with other embodiments described herein, the size of the first region along a reference direction may be from 1% to 70%, for example 50% of the size of the aperture plate along the reference direction. In the exemplary case of a first region 1310 and an aperture plate 230 each having the shape of a disc, as illustrated in e.g. FIG. 13a, the size of the first region along the reference direction may be the diameter of the first region and the size of the aperture plate along the reference direction may be the diameter of the aperture plate.

Topographic contrast can be optimized by adjusting the size of region 1310 by the lens system 222 and 224. For a reduced size, e.g. 10%-25% of the size of the aperture plate, only electrons with large starting angle on the wafer are detected on the outer diodes on the cost of signal intensity. For a large size of region 1310, e.g. 40%-70% of the size of the aperture plate, a large portion of starting angles on the wafer is collected on the outer diodes, increasing signal intensity and potentially decreasing topographic contrast. Depending on the feature to be detected, one or the other setting may be beneficial.

In the topography detection mode, the secondary charged particle beam 140 being mapped onto the first region 1310, as illustrated in FIG. 13a, may enter the central opening 520, the first opening 232, the second opening 234 as well the further openings 836 and 838. Accordingly, during the topography detection mode, the first secondary charged particle sub-beam may pass through the first opening 232, the second secondary charged particle sub-beam may pass through the second opening 234 and/or the third secondary charged particle sub-beam may pass through the central opening 520, as described above. Further sub-beams of the secondary charged particle beam 140 may pass through the further openings 836 and 838 shown in FIG. 13a.

FIG. 13b shows the secondary charged particle beam 140 passing through the aperture plate 230 in the bright field detection mode. In the bright field detection mode, the secondary charged particle beam 140 is mapped onto a second region 1320 of the aperture plate 230 independent of a variation of the at least one second operating parameter. The second region may correspond to the cross-section, with respect to the drawing plane, of the secondary charged particle beam passing through the aperture plate in the bright field detection mode, independent of a variation of the at least one second operating parameter.

The exemplary second region 1320 shown in FIG. 13b has substantially the shape of a disc. As shown, the second region 1320 has a boundary 1322 which, for the exemplary second region 1320 shown in FIG. 13b, is a circular boundary. The second region 1320 shown in FIG. 13b may correspond to a disc-shaped cross-section, with respect to the drawing plane, of the secondary charged particle beam 140 passing through the aperture plate 230 in the bright field detection mode.

As shown in FIG. 13b, the cross-section of the central opening 520 with respect to the drawing plane contains the second region 1320. The second region 1320 shown in FIG. 13b does not overlap or does essentially not overlap with the first opening 232, nor with the second opening 234, nor with either one of the further openings 836 and 838. Accordingly, in the bright field detection mode, the secondary charged particle beam 140 enters the central opening 520 but does not enter the first opening 232 nor the second opening 234 nor either one of the further openings 836 and 838. In the bright field detection mode, the secondary charged particle beam 140 may pass entirely through the central opening 520.

Figure 14:
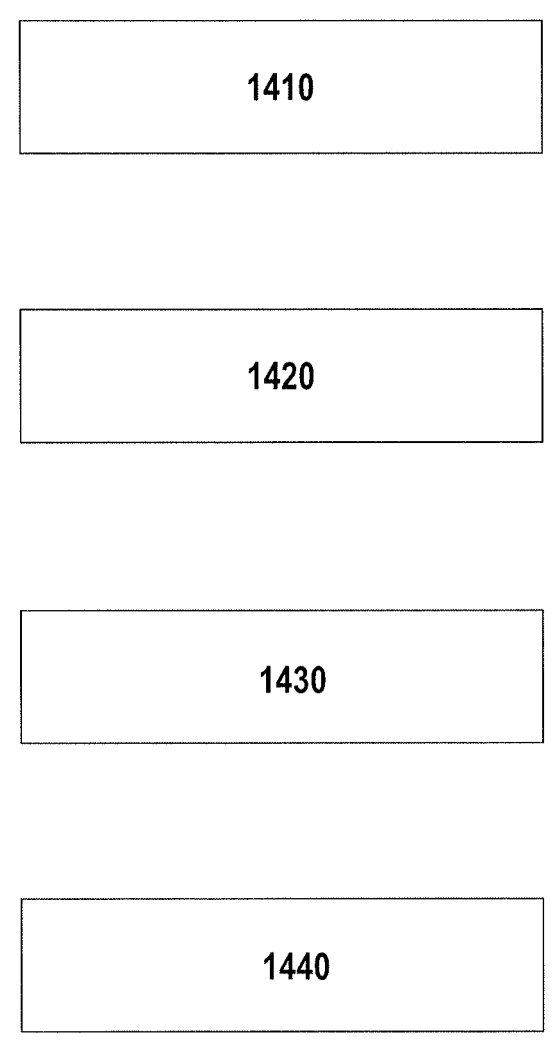

According to a further embodiment, and as illustrated in FIG. 14, a method of imaging a secondary charged particle beam emanating from a sample by impingement of a primary charged particle beam is provided. As indicated in FIG. 14 with reference numeral 1410, the method includes setting a first operating parameter, as described herein, to a first value. The method further includes controlling, while the first operating parameter is set to the first value, the excitation of a first lens and of a second lens to map the secondary charged particle beam onto a first region on an aperture plate, as indicated in FIG. 14 with reference numeral 1420. The first lens and the second lens may be included in a lens system as described herein. The first region overlaps with a first opening of the aperture plate and with a second opening of the aperture plate. As indicated in FIG. 14 with reference numeral 1430, the method further includes setting the first operating parameter to a second value different from the first value. The method further includes controlling, while the first operating parameter is set to the second value, the excitation of the first lens and of the second lens to map the secondary charged particle beam onto the first region on the aperture plate, as indicated in FIG. 14 with reference numeral 1440.

According to embodiments, which can be combined with other embodiments described herein, the first region may overlap with a central opening of the aperture plate as described herein. The secondary charged particle beam may be mapped onto the first region on the aperture plate in a topography detection mode, as described herein.

The first opening and/or the second opening may partially overlap with the first region, as e.g. shown in FIG. 13a. The aperture plate may define an aperture plate plane. For example, with respect to the embodiments illustrated in FIGS. 13a-13b, the aperture plate plane may refer to the drawing plane. The first region may be contained in the aperture plate plane. The optical axis defined by the aperture plate may extend through a center of the first region. The aperture plate plane may extend through the first opening, through the second opening and/or through the central opening. As shown in FIG. 13a, a portion of the cross-section of the first opening with respect to the aperture plate plane may be contained in the first region. As further shown in FIG. 13a, a further portion of the cross-section of the first opening with respect to the aperture plate plane may lie outside of the first region. Similarly, a portion of the cross-section of the second opening with respect to the aperture plate plane may be contained in the first region. A further portion of the cross-section of the second opening with respect to the aperture plate plane may lie outside of the first region. The cross-section of the central opening with respect to the aperture plate plane may be contained in the first region, as shown in FIG. 13a.

According to some embodiments, which can be combined with other embodiments described herein, the method further includes setting a second operating parameter, as described herein, to a third value. The method further includes controlling, while the second operating parameter is set to the third value, the excitation of the first lens and of the second lens to map the secondary charged particle beam onto a second region on the aperture plate. The second region fully overlaps with the central opening and is contained in the first region. That is the second region is within the central opening or equals the central opening. Accordingly, the second region does not extend beyond the central opening, i.e. fully overlaps with the central opening.

The secondary charged particle beam may be mapped onto the second region on the aperture plate in a bright field detection mode, as described herein. The optical axis defined by the aperture plate may extend through a center of the second region. The second region may be different from the first region.

The second region may be contained in the aperture plate plane. According to embodiments, which can be combined with other embodiments described herein, the area of the second region may be substantially the same as the cross-sectional area of the central opening with respect to the aperture plane. The terminology of the two areas being "substantially the same" may refer to a ratio of the two areas lying in the range from 0.01 to 1.1. The area of the second region may be from 1% to 110% of the area of the central opening. According to embodiments, which can be combined with other embodiments, and as illustrated in FIG. 13b, the second region may be contained in the cross-section of the central opening with respect to the aperture plate plane. No portion of the secondary charged particle beam may pass through the aperture plate outside of the central opening.

The first opening and/or the second opening may be distanced from the second region and/or may not overlap with the second region.

According to embodiments, which can be combined with other embodiments described herein, the second operating parameter may be the same as the first operating parameter. The third value may be the same as the first value or may be different from the first value. The third value may be the same as the second value or may be different from the second value.

According to embodiments, which can be combined with other embodiments described herein, the second operating parameter may be different from the first operating parameter.

According to embodiments, which can be combined with other embodiments described herein, the first operating parameter is the magnetic field strength of the objective lens. Controlling the excitation of the first lens and of the second lens, while the first operating parameter is set to the second value, includes compensating, relative to the situation where the first operating parameter is set to the first value, a Larmor rotation of the secondary charged particle beam. Therein, the Larmor rotation may be compensated by a magnetic field of the first lens, by a magnetic field of the second lens or by magnetic fields of both the first lens and the second lens.

While the foregoing is directed to some embodiments of the invention, other and further embodiments may be devised without departing from the scope determined by the claims that follow.

The invention claimed is:

1. A method of imaging a secondary charged particle beam emanating from a sample by impingement of a primary charged particle beam, the method comprising:
setting a first operating parameter to a first value, the first operating parameter selected from a group comprising: landing energy of the primary charged particle beam on the sample, extraction field strength for the secondary charged particle beam at the sample, magnetic field strength of an objective lens that focuses the primary charged particle beam onto the sample, and working distance of the objective lens from the sample;
controlling, while the first operating parameter is set to the first value, an excitation of a first lens to a first excitation value of the first lens and an excitation of a second lens to a first excitation value of the second lens to map the secondary charged particle beam onto a region of a first size on an aperture plate in a topography detection mode, wherein the region of the first size overlaps with a first opening of the aperture plate and with a second opening of the aperture plate, wherein the first excitation value of the first lens and the first excitation value of the second lens are each controlled individually to adjust an opening angle of the secondary charged particle beam in two dimensions to provide the secondary charged particle beam onto the region of the first size, and the aperture plate separates the secondary charged particle beam into secondary charged particle sub-beams corresponding to the first opening of the aperture plate and the second opening of the aperture plate;
setting the first operating parameter to a second value different from the first value;
controlling, while the first operating parameter is set to the second value, the excitation of the first lens to a second excitation value of the first lens and the excitation of the second lens to a second excitation value of the second lens to map the secondary charged particle beam onto the region of the first size on the aperture plate in the topography detection mode, wherein the second excitation value of the first lens and the second excitation value of the second lens are each controlled individually to adjust the opening angle of the secondary charged particle beam in two dimensions to provide the secondary charged particle beam onto the region of the first size, and wherein the first excitation value of the first lens is different from the second excitation value of the first lens, and the first excitation value of the second lens is different from the second excitation value of the second lens;

setting the first operating parameter to a third value different from the first and second values; and controlling, while the first operating parameter is set to the third value, the excitation of the first lens to a third excitation value of the first lens and the excitation of the second lens to a third excitation value of the second lens to map the secondary charged particle beam onto a region of a second size on the aperture plate in the topography detection mode, wherein the region of the second size overlaps with the first opening and with the second opening, wherein the third excitation value of the first lens and the third excitation value of the second lens are each controlled individually to adjust the opening angle of the secondary charged particle beam in two dimensions to provide the secondary charged particle beam onto the region of the second size, wherein the second size is different from the first size.

2. The method according to claim 1, wherein the region of the first size also overlaps with a central opening of the aperture plate, wherein the first opening and the second opening are located radially outward from the central opening with respect to an optical axis that is defined by the aperture plate.

3. The method according to claim 2, further comprising:

setting a second operating parameter to a third value, the second operating parameter selected from a group comprising: landing energy of the primary charged particle beam on the sample, extraction field strength for the secondary charged particle beam at the sample, magnetic field strength of an objective lens that focuses the primary charged particle beam onto the sample, and working distance of the objective lens from the sample; and controlling, while the second operating parameter is set to the third value, the excitation of the first lens and the excitation of the second lens to map the secondary charged particle beam onto a second region on the aperture plate, the second region fully overlapping with the central opening and being contained in the region of the first size.

4. The method of claim 1, wherein the first operating parameter is the magnetic field strength of the objective lens, and wherein controlling the excitation of the first lens and the excitation of the second lens, while the first operating parameter is set to the second value, comprises compensating, relative to a situation where the first operating parameter is set to the first value, a Larmor rotation of the secondary charged particle beam by a magnetic field of the first lens, by a magnetic field of the second lens or by magnetic fields of both the first lens and the second lens.

* * * * *